(12) United States Patent
Russell et al.

(10) Patent No.: US 7,297,113 B1
(45) Date of Patent: Nov. 20, 2007

(54) MICROSENSOR SYSTEM AND METHOD FOR MEASURING DATA

(75) Inventors: Stephen D. Russell, San Diego, CA (US); Paul R. de la Houssaye, San Diego, CA (US); Jamie K. Pugh, San Diego, CA (US); William Pugh, San Diego, CA (US); Dennis E. Amundson, San Diego, CA (US); Howard W. Walker, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 725 days.

(21) Appl. No.: 10/872,131

(22) Filed: Jun. 18, 2004

Related U.S. Application Data

(60) Division of application No. 10/762,133, filed on Jan. 20, 2004, and a continuation-in-part of application No. 10/655,631, filed on Aug. 29, 2003, now abandoned, and a continuation-in-part of application No. 10/423,568, filed on Apr. 25, 2003.

(60) Provisional application No. 60/465,298, filed on Apr. 25, 2003.

(51) Int. Cl.
*A61B 5/07* (2006.01)

(52) U.S. Cl. .................. 600/302; 600/361; 600/364

(58) Field of Classification Search .............. 600/345, 600/354, 506, 302, 544, 473, 475, 322, 361, 600/364, 485; 204/153.1; 378/62; 250/458.1, 250/201.1
See application file for complete search history.

(56) References Cited

U.S. PATENT DOCUMENTS

| 4,534,825 | A | * | 8/1985 | Koning et al. ............... 438/49 |
|---|---|---|---|---|
| 4,716,887 | A | * | 1/1988 | Koning et al. ............... 607/24 |
| 5,064,618 | A | * | 11/1991 | Baker et al. ............. 422/82.01 |
| 5,405,510 | A | * | 4/1995 | Betts et al. ................. 205/782 |
| 5,837,446 | A | * | 11/1998 | Cozzette et al. ............... 435/6 |
| 6,554,982 | B1 | * | 4/2003 | Shin et al. .................. 204/401 |
| 2002/0049389 | A1 | * | 4/2002 | Abreu ........................ 600/558 |
| 2002/0087057 | A1 | * | 7/2002 | Lovejoy et al. ............. 600/349 |
| 2005/0101841 | A9 | * | 5/2005 | Kaylor et al. ............... 600/300 |

* cited by examiner

Primary Examiner—Charles A. Marmor, II
Assistant Examiner—Anita Saidi
(74) Attorney, Agent, or Firm—Peter A. Lipovsky; J. Eric Anderson; Allan Y. Lee

(57) ABSTRACT

One embodiment is a microprobe. An example of the microprobe comprises a housing having an aperture. This example of the microprobe also comprises an ISFET attached to the housing. The ISFET may have a gate located proximate the aperture. This example of the microprobe further comprises a reference electrode attached to the housing proximate the aperture. Another embodiment is a microsensor system. Another embodiment is a method for measuring a characteristic of tissue. Yet another embodiment is a method for monitoring tissue pH.

2 Claims, 21 Drawing Sheets

Full Staff Days:

| Date | Daily Incidence | Mean | Std. Dev. | Trend Direction | Trend Length | Statistically Significant Event |
|---|---|---|---|---|---|---|
| 2002-05-10 | 0 | 2.8571 | 8.8806 | | | |
| 2002-05-11 | 0 | 2.8571 | 8.8806 | | | |
| 2002-05-12 | 0 | 2.8571 | 8.8806 | | | |
| 2002-05-13 | 1 | 2.8571 | 8.8806 | increasing | 1 | |
| 2002-05-14 | 7 | 2.8571 | 8.8806 | increasing | 2 | |
| 2002-05-15 | 7 | 2.8571 | 8.8806 | increasing | 3 | |
| 2002-05-16 | 5 | 2.8571 | 8.8806 | increasing | 4 | |
| 2002-05-17 | 19 | 2.8571 | 8.8806 | increasing | 5 | |
| 2002-05-18 | 96 | 2.8571 | 8.8806 | increasing | 6 | positive burst |
| 2002-05-19 | 0 | 2.8571 | 8.8806 | increasing | | positive trend |
| 2002-05-20 | 0 | 2.8571 | 8.8806 | increasing | | |
| 2002-05-21 | 0 | 2.8571 | 8.8806 | | | |
| 2002-05-22 | 0 | 2.8571 | 8.8806 | | | |
| 2002-05-23 | 0 | 2.8571 | 8.8806 | | | |
| 2002-05-24 | 0 | 2.8571 | 8.8806 | | | |
| 2002-05-25 | 0 | 2.8571 | 8.8806 | | | |
| 2002-05-26 | 0 | 2.8571 | 8.8806 | | | |

FIG. 9

SHEWHART CUSUM, SYSTOLIC, PATIENT 4

| TIME | INPUT | NORMAL | SD | Z | SL(I) | SH(I) | INDICATOR | EVENT | SIGNAL SHIFT LENGTH | PREDICTED X | CONFIDENCE INTERVAL LOWER | UPPER |
|---|---|---|---|---|---|---|---|---|---|---|---|---|
| 0. | 136.00 | 134.6667 | 6.1101 | 0.19 | 0.00 | 0.00 | | | 0 | 0.00 | | |
| 14. | 128.00 | 134.6667 | 6.1101 | -0.94 | 0.08 | 0.00 | - | | 1 | -4.00 | | |
| 35. | 140.00 | 134.6667 | 6.1101 | 0.76 | 0.00 | 0.26 | + | | 1 | 5.33 | 140.00 127.78 | 152.22 |
| 56. | 142.00 | 134.6667 | 6.1101 | 1.04 | 0.00 | 0.80 | + | | 2 | 6.33 | 141.00 128.78 | 153.22 |
| 98. | 112.00 | 134.6667 | 6.1101 | -3.21 | 2.71 | 0.00 | - | negative burst | 1 | -22.67 | 148.91 99.78 | 124.22 |
| 112. | 160.00 | 134.6667 | 6.1101 | 3.59 | 0.00 | 3.09 | + | positive burst | 1 | 25.33 | 160.00 147.78 | 172.22 |
| 126. | 156.00 | 134.6667 | 6.1101 | 3.02 | 0.00 | 5.61 | + | positive burst | 2 | 23.33 | 158.00 145.78 | 170.22 |
| 154. | 140.00 | 134.6667 | 6.1101 | 0.76 | 0.00 | 5.87 | + | positive trend | 3 | 17.33 | 152.00 139.78 | 164.22 |
| 189. | 140.00 | 134.6667 | 6.1101 | 0.76 | 0.00 | 6.13 | + | | 4 | 14.24 | 148.91 136.69 | 161.13 |
| 245. | 144.00 | 134.6667 | 6.1101 | 1.32 | 0.00 | 6.95 | + | | 5 | 13.36 | 148.03 135.81 | 160.25 |
| 280. | 144.00 | 134.6667 | 6.1101 | 1.32 | 0.00 | 7.77 | + | | 6 | 13.25 | 147.92 135.70 | 160.14 |
| 301. | 146.00 | 134.6667 | 6.1101 | 1.61 | 0.00 | 8.88 | + | | 7 | 13.22 | 147.89 135.67 | 160.11 |
| 336. | 130.00 | 134.6667 | 6.1101 | -0.66 | 0.16 | 7.72 | + | | 8 | 11.86 | 146.53 134.31 | 158.75 |
| 371. | 160.00 | 134.6667 | 6.1101 | 3.59 | 0.00 | 10.81 | + | positive burst | 9 | 12.39 | 147.06 134.83 | 159.28 |
| 399. | 152.00 | 134.6667 | 6.1101 | 2.46 | 0.00 | 12.76 | + | positive outlier | 10 | 13.02 | 147.69 135.47 | 159.91 |
| 455. | 140.00 | 134.6667 | 6.1101 | 0.76 | 0.00 | 13.02 | + | | 11 | 13.30 | 147.97 135.75 | 160.19 |
| 490. | 148.00 | 134.6667 | 6.1101 | 1.89 | 0.00 | 14.41 | + | | 12 | 13.31 | 147.98 135.76 | 160.20 |
| 553. | 110.00 | 134.6667 | 6.1101 | -3.50 | 3.00 | 10.41 | + | negative burst | 12 | 16.81 | 151.48 139.26 | 163.70 |
| 595. | 140.00 | 134.6667 | 6.1101 | 0.76 | 0.00 | 10.67 | + | | 13 | 11.73 | 146.39 134.17 | 158.61 |

MICROSENSOR SYSTEM AND METHOD FOR MEASURING DATA

CROSS-REFERENCE TO RELATED APPLICATIONS

This application is a divisional application of U.S. patent application Ser. No. 10/762,133, filed 20 Jan. 2004, titled "Microsensor System and Method for Measuring Data", pending, which claims the benefit of U.S. Provisional Patent Application No. 60/465,298, filed 25 Apr. 2003, titled "Method and Apparatus for Medical Data Surveillance", both of which are incorporated herein by this reference. U.S. patent application Ser. No. 10/762,133 is a continuation-in-part of U.S. patent application Ser. No. 10/423,568, filed 25 Apr. 2003, titled "Method and System for Detecting Changes in Data", pending, and is a continuation-in-part of U.S. patent application Ser. No. 10/655,631, filed 29 Aug. 2003, titled "System and Method for Improved Patient Status Monitoring", now abandoned, both of which are incorporated herein by this reference.

BACKGROUND

1. Technical Field

The present invention relates to monitoring data, and in some embodiments may concern assessing the medical condition of a patient. More particularly, some examples of the invention concern using a subcutaneous sensor to measure a characteristic of tissue in a patient, and in some examples may be used to measure tissue pH to detect shock, or to determine if tissue is viable.

2. Description of Related Art

Improved casualty/patient care is vital to military operational practices, and is also of great importance in many civilian environments. For example, frequently it is important for a medical care provider to be able to quickly and accurately assess the medical condition of a patient in a combat environment, during disaster relief, at an accident scene, during patient transport, in an emergency room, at a hospital, or at any other location during a medical emergency or the general treatment of a patient.

Shock is one of the body's biochemical reactions to an injury. The presence of hypoglycemic or hemorrhagic shock, which frequently occurs in combat casualties and accident victims, must be rapidly and accurately assessed, and must be monitored, to ensure the best prognosis, final patient disposition, and maximum survival rates.

Detecting depression of a patient's vital signs (blood pressure, respiration and heart rate), is a known method for detecting shock. This technique may be used in the field and other environments. However, this method is imprecise and is not favored if other methods are available.

Two methods are known that generally have been used for monitoring the shock state of a patient in a hospital environment. In the first method, global blood flow assessments are made by measuring arterial $P_a(O_2)$ oxygen delivery to the body. In the second method, arterial blood lactate concentrations and oxygen consumption are measured. Both of these techniques are invasive and hence may negatively impact the patient's health, because they generally require drawing blood with a catheter (perhaps from the stomach), and also require sophisticated equipment, and consequently cannot be used in the field.

Tissue tonometry is a tissue oriented approach to measuring and diagnosing the shock state of a patient. Tissue $P(O_2)$ levels, tissue $P(CO_2)$ levels, and tissue pH, have been shown to be reliable estimates of a compensated shock state. However, the use of these approaches has been hampered by the lack of a reliable and noninvasive method of obtaining accurate measurements.

In combat, disaster, and accident scenarios, the extent of injury to a patient may be so severe as to require amputation of gangrenous tissue. Gangrenous tissue is tissue that has died due to lack of blood supply. Dead tissue may also be present on frostbite victims. Generally, the goal of an amputation is to remove all dead tissue. The extent of tissue removal during an amputation may be excessive, because medical personnel lack an accurate means of determining the demarcation between viable and non-viable tissue.

In summary, known methods of measuring the shock state of a patient are inadequate because they are invasive, non-portable, and/or inaccurate. Further, known methods for identifying and monitoring the border between viable and non-viable tissue are not sufficiently accurate to preclude needless amputation of viable tissue. Additionally, there is no known means of monitoring the continued viability of tissue after an amputation.

SUMMARY

One embodiment is a microprobe. An example of the microprobe comprises a housing having an aperture. This example of the microprobe also comprises an ISFET attached to the housing. The ISFET may have a gate located proximate the aperture. This example of the microprobe further comprises a reference electrode attached to the housing proximate the aperture.

Other embodiments are described in the sections below, and include, for example, a microsensor system, a microsensor array system, a method for monitoring data (which in some examples may be a characteristic of tissue), and a signal bearing medium tangibly embodying a program of machine-readable instructions executable by a digital processing apparatus to perform a method for monitoring data (which is some examples may be a characteristic of tissue).

Some embodiments provide for portably, noninvasively, and accurately measuring and monitoring the shock state of a patient, and further, some embodiments may accurately identify viable and non-viable tissue.

BRIEF DESCRIPTION OF THE DRAWINGS

FIG. 9 is a data analysis report in accordance with an exemplary embodiment.

FIG. 10 is another example data analysis report in accordance with an exemplary embodiment.

DETAILED DESCRIPTION

Figure 1:
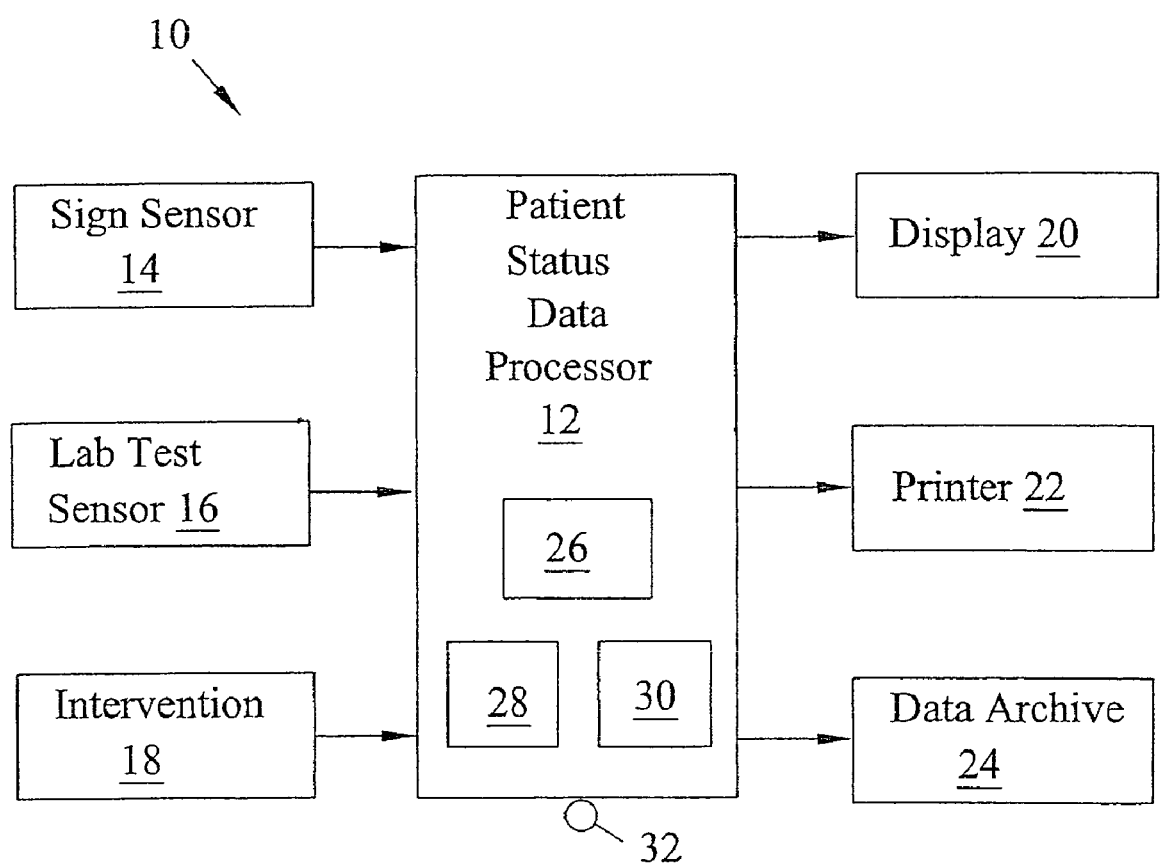
FIG. 1 is a block diagram of the hardware components and interconnections of a patient status monitor in accordance with an exemplary embodiment.

The nature, objectives, and advantages of the invention will become more apparent to those skilled in the art after considering the following detailed description in connection with the accompanying drawings.

I. Introduction

The present invention generally relates to monitoring data. Some embodiments provide a microvascular technique for measuring a characteristic of tissue in a patient. Some specific examples concern injecting a microprobe in dermal tissue, to quickly and relatively non-invasively measure dermal tissue pH. Although an embodiment for measuring tissue pH is discussed in this introduction, the invention is not limited to this specific illustrative example.

Real-time measurement of dermal tissue pH (the pH of the vascular layer of the skin), can be used to monitor the general onset of shock. Some examples of the invention provide a real-time microsensor system for measuring tissue pH in the vascular layer of skin, and consequently may be used to detect and provide an early warning for the onset of hypoglycemic or hemorrhagic shock. Thus, the microsensor system provides a relatively non-invasive, portable instrument for monitoring the general onset of shock. The microprobe may be implanted in the dermis in almost any location on a human body, including the fingers and toes, which are desirable locations for measuring shock.

The microsensor system may also be used to identify viable tissue, for example before, during, and/or after an amputation or other surgery. One important application is identifying and/or monitoring viable and non-viable tissue in frostbite patients. Another important application is identifying and/or monitoring gangrenous and non-gangrenous tissue. Another application is identifying and/or monitoring non-viable tissue after a patient has been exposed to severe radiation. In circumstance where non-viable tissue must be amputated, a plurality of microprobes could be placed in different locations in patient tissue, to gather information that may be presented as a three dimensional representation of the patient tissue, so that a surgeon can determine precisely which tissue to remove (and also which tissue that possibly may be revived).

The microsensor system could also be used to determine whether there is adequate capillary fill after removing a tourniquet. In another example, the microsensor system could be used to detect and/or monitor indicators of heart blockage (may be indicated by no change after implementation of an intervention) or congestive heart failure. Statistical algorithms may be performed using data gathered over a period of time, to identify trends and other useful information in the data.

As an example, the microsensor system with or without the patient status monitor could be routinely used by medics and corpsmen on the battlefield, and also could be used by surgeons and other personnel at forward medical units. The microsensor system with or without the patient status monitor could also be used in disaster scenarios, and by emergency medical teams. The microsensor system with or without the patient status monitor could be used to assist in establishing patient triage, and generally could result in improved urgent care and increased patient survival rates. The microsensor system and the patient status monitor generally provide enhanced functionality, sensitivity, and accuracy.

II. Definitions

The following acronyms and definitions are used herein:

Acronyms:

Ag—Silver

AgCl—Silver Chloride

Al—Aluminum

CD-ROM—Compact Disc-Read Only Memory

CD-R—Compact Disc-Read

CD-RW—Compact Disc-Read Write

CUSTUM—Cumulative Sum

DVD-R—Digital Versatile/Video Disc Recorable (write once storage)

DVD+R—Digital Versatile/Video Disc Recorable (write once storage)

DVD-RW—Digital Versatile/Video Disc Read/Write (write multiple times storage)

DVD+RW—Digital Versatile/Video Disc Read/Write (write multiple times storage)

EPROM—Erasable Programmable Read-Only Memory

EEPROM—Electrically Erasable Programmable Read-Only Memory

FIR CUSUM—Fast Initial Response Cumulative Sum

FIR MAX CUSUM—Fast Initial Response Maximum Cumulative Sum

ICD-9—International Classification of Diseases-Revision 9

ISFET—Ion Sensitive Field Effect Transistor

MAX CUSUM—Maximum Cumulative Sum

MEMS—MicroElectroMechanical System

MOSFET—Metal-Oxide-Semiconductor Field Effect Transistor

RAID—Redundant Array of Inexpensive Discs

RAMAC—Random Access Method of Accounting and Control

RAM—Random Access Memory

ROM—Read Only Memory

Si—Silicon $Si_3N_4$—Silicon Nitride $SiO_2$—Silicon Dioxide

SOI—Silicon-On-Insulator

SOS—Silicon-On-Sapphire

WORM—Write Once Read Many (write once storage)

Definitions:

β (Beta):

β is a constant, $\mu_2/(2\sigma)$, the minimum number of standard deviations from the mean the Markov sums will pick up a change in state. As an example, β may be set equal to 0.5

Baseline:

The baseline is an estimate of the background noise only condition.

Burst point:

δ and γ are the Shewhart test thresholds where γ>δ, for example, δ equals 2 and γ equals 3. A burst point is a data point at least γ standard deviations away from the baseline mean. (The test is adjusted for small sample sizes.)

Data point i (or $x_i$):

The ith data input set associated with a data type consisting of a data, time, and value.

Data type:

Type of data analyzed such as pulse rate, blood pressure, respiration, body temperature, or white blood cell count for which there is information for a patient.

δ (Delta):

δ and γ are the Shewhart test thresholds where γ>δ, for example, δ equals 2 and γ equals 3.

$\bar{\omega}$ is the approximate ratio of the standard normal threshold and the t-test threshold associated with the degrees of freedom in the mean and standard deviation calculations. $\bar{\omega}$ is calculated as follows:

$$\bar{\omega} = \sqrt{\frac{n-r}{n-r+1}}$$

F:

F is the noise only distribution and f is the derivative of F in the derivation of the cumulative sum statistics.

FIRSH:

FIRSH is the Fast Initial Response cumulative upper sum.

FIRSH max:

FIRSH max is the Fast Initial Response Maximum cumulative upper sum.

FIRSL:

FIRSL is the Fast Initial Response cumulative lower sum.

FIRSL max:

FIRSL max is the Fast Initial Response Maximum cumulative lower sum.

G:

G is the noise plus signal distribution and g is the derivative of G in the derivation of the cumulative sum statistics.

γ (Gamma):

δ and γ are the Shewhart test thresholds where γ>δ, for example, δ equals 2 and γ equals 3.

H:

H is the CUSUM statistic test threshold. H is a constant chosen such that the reciprocal of the average run length equals the desired probability of false alarm.

Input data:

The data associated with a data type for a particular patient. Input data may consist of sets of date, time, and value information.

K:

Index of the data point where the signal starts.

L:

Index of the data point where the signal ends.

m:

m is a positive integer that represents the number of data points that have been input and received into the process.

Mean:

The mean is the average of the conforming data points and is calculated using the formula:

$$\text{mean} = \frac{\sum_{i=1}^{m} R(x_i)}{m-r}$$

μ (Mu):

Mu is the population mean.

n:

The number of data points used to create the currently in-use baseline mean and standard deviation.

$N(\mu_1, \sigma^2)$:

$N(\mu_1, \sigma^2)$ normal distribution with mean $\mu_1$ and standard deviation σ.

$N(\mu_2, \sigma^2)$:

$N(\mu_2, \sigma^2)$ normal distribution with mean $\mu_2$ and standard deviation σ.

Outlier:

δ and γ are the Shewhart test thresholds where γ>δ, for example, δ equals 2 and γ equals 3. A outlier is a data point at least δ standard deviations away from the baseline mean. (The test is adjusted for small sample sizes.)

r:

The number of data points removed from consideration either a priori by the end-user or because they are found to be non-conforming data points.

$R(X_i)$:

The function of the incoming observations $R(X_i)$, is used to remove user specified and non-conforming data points from the baseline calculation $$\sqrt{\frac{i-r}{i-r+1}}\left|\frac{X_i - \text{mean}}{sd}\right| \geq 2$$

or if the user has specified that $x_i$ is to be removed; and is equal to $x_i$, otherwise.

S:

S is the cumulative sum associated with unspecified F and G distributions in the cumulative sum statistic derivation.

sd:

sd is the standard deviation and is calculated using the formula:

$$sd = \sqrt{\frac{\sum_{i=1}^{m}(R(x_i) - \text{mean})^2}{m - r - 1}}$$

SH:

SH is the CUSUM upper sum and for the ith data-point is calculated as follows:

$$SH_i = \max(SH_{i-1} + \hat{t}_i - \beta, 0)$$

The Fast Initial Response statistic is created by initializing the cumulative sum to H/2.

SH max:

SH max is the MAX CUSUM upper sum statistic and for the ith data-point is calculated as follows:

$$sd = \sqrt{\frac{\sum_{i=1}^{m}(R(x_i) - \text{mean})^2}{m - r - 1}}$$

where $SH_0 = 0$.

The Fast Initial Response statistic is created by initializing the cumulative sum to H/2.

$\text{Shift}_{i, lower}$:

The negative signal amplitude or downward shift for the ith data point is estimated as follows:

$$\text{shift}_{i,lower} = \left(\frac{SL_i}{\text{length}_{i,lower}} + \beta\right)(f)(sd)$$

$\text{Shift}_{i, upper}$:

The positive signal amplitude or upward shift for the ith data point is estimated as follows:

$$\text{shift}_{i,upper} = \left(\frac{SH_i}{\text{length}_{i,upper}} + \beta\right)(f)(sd)$$

δ (Sigma)

Sigma is the population standard deviation.

SL:

SL is the CUSUM lower sum and for the ith data-point is calculated as follows:

$$SL_i = \max(SL_{i-1} \hat{t}_i - \beta, 0)$$

The Fast Initial Response statistic is created by initializing the cumulative sum to H/2.

SL max:

SL max is the MAX CUSUM lower sum statistic and for the ith data-point is calculated as follows:

$$SL\max_j = \max_{i=1,\ldots j}(SL_i)$$

where $SL_0 = 0$.

The Fast Initial Response statistic is created by initializing the cumulative sum to H/2.

S max:

S max is the maximum cumulative sum associated with unspecified F and G distributions.

t:

t is the standard score. The approximate standard score is calculated as follows:

$$\hat{t}_i = (\varpi)\left(\frac{X_i - \text{mean}}{sd}\right)$$

III. Hardware Components and Interconnections

A. Patient Status Monitor

Before discussing the hardware and the operation of a microsensor system, below, an embodiment of an apparatus for monitoring data will first be discussed. As a specific example of this apparatus, an apparatus for monitoring patient status will be discussed. With some modifications to the example below, it is understood that "patient" status can in some cases additionally be more generally understood as the status of the system that is being monitored, which may include, for example, a manufacturing environment and the data produced from such for quality control, the stock market or other economic systems, or a population group (which may include plants, bacteria, etc.) being monitored for disease or exposure to agents injurious to their or its health. The apparatus for monitoring patient status may be used in conjunction with, or may be incorporated into, the microsensor system. As an example, the apparatus for monitoring patient status may be embodied by the hardware components and interconnections of the patient status monitor 10 shown in FIG. 1. The patient status monitor 10 includes a patient status data processor 12.

One or more data collection devices are coupled to the patient status data processor 12, for sensing or otherwise receiving data. As an example, the data collection devices may include one or more medical sign sensors 14, one or more medical lab data test sensors 16, and/or one or more intervention data collectors 18. One or more of the medical sign sensors 14 may be a microprobe 1302 (shown in FIG. 13), or a microprobe system 1300 (shown in FIG. 13), (which may gather tissue pH information and possibly other information), and which will be discussed below.

The patient status data processor 12 may be coupled to one or more output devices, which may include, for example, one or more displays 20, one or more printers 22, and/or one or more data archives 24. Display 20 may include a visible and/or audible alarm and/or other means to convey an alarm condition. For example, the display may include a speaker or buzzer or other audio transducer for producing an audio alarm. As another example, a visible alarm may be presented on the display, or a LED could be included on the display housing for indicating an alarm. The medical sign sensor 14 and medical lab data test sensors 16 sense or otherwise receive information such as, for example the following data types, pulse rate, blood pressure, respiration, body temperature, white blood cell count, iron, cholesterol, triglyceride, blood sugar, tissue pH, and blood gas information for a patient, and output data values representative of the medical signs and lab tests, as data to the patient status data processor 12. The intervention data collector 18 gathers information concerning actions taken to correct problems, upper and lower patient reference values, upper and lower patient threshold values, and other significant actions as well as how long a data type value can remain unchanged before an alarm should sound that an intervention is not working. For example, the intervention data collector 18 may receive data concerning when medication is administered or when the patient was covered with a blanket. The intervention data may be date/time stamped.

The patient status data processor 12 may be any type of data processing apparatus, and as an example, may be a microprocessor or computer. The computer may be, for example, a personal computer, personal digital assistant, mainframe computer, computer workstation, supercomputer, or other suitable machine. As shown in FIG. 1, the patient status data processor 12 may include a processor 26, such as a microprocessor or other processing machine, which may be coupled to a memory 28 and a nonvolatile storage 30. The memory 28 may comprise random access memory, and may be used to store programming instructions executed by the processor 26. The nonvolatile storage 30 may comprise, for example, one or more magnetic data storage disks such as a "hard drive," an optical drive, a tape drive, or any other suitable storage device. The patient status data processor 12 may also include an input/output 32, such as a line, bus, cable, or electromagnetic link, for the data processor 12 to receive instructions from a user, and may also permit exchanging data with locations external to the patient status data processor 12. Alternatively, the memory 28 and/or the nonvolatile storage 30 may be eliminated, and further, memory and/or nonvolatile storage may be provided on-board the processor 26, or externally to the patient status data processor 12.

Figure 2:
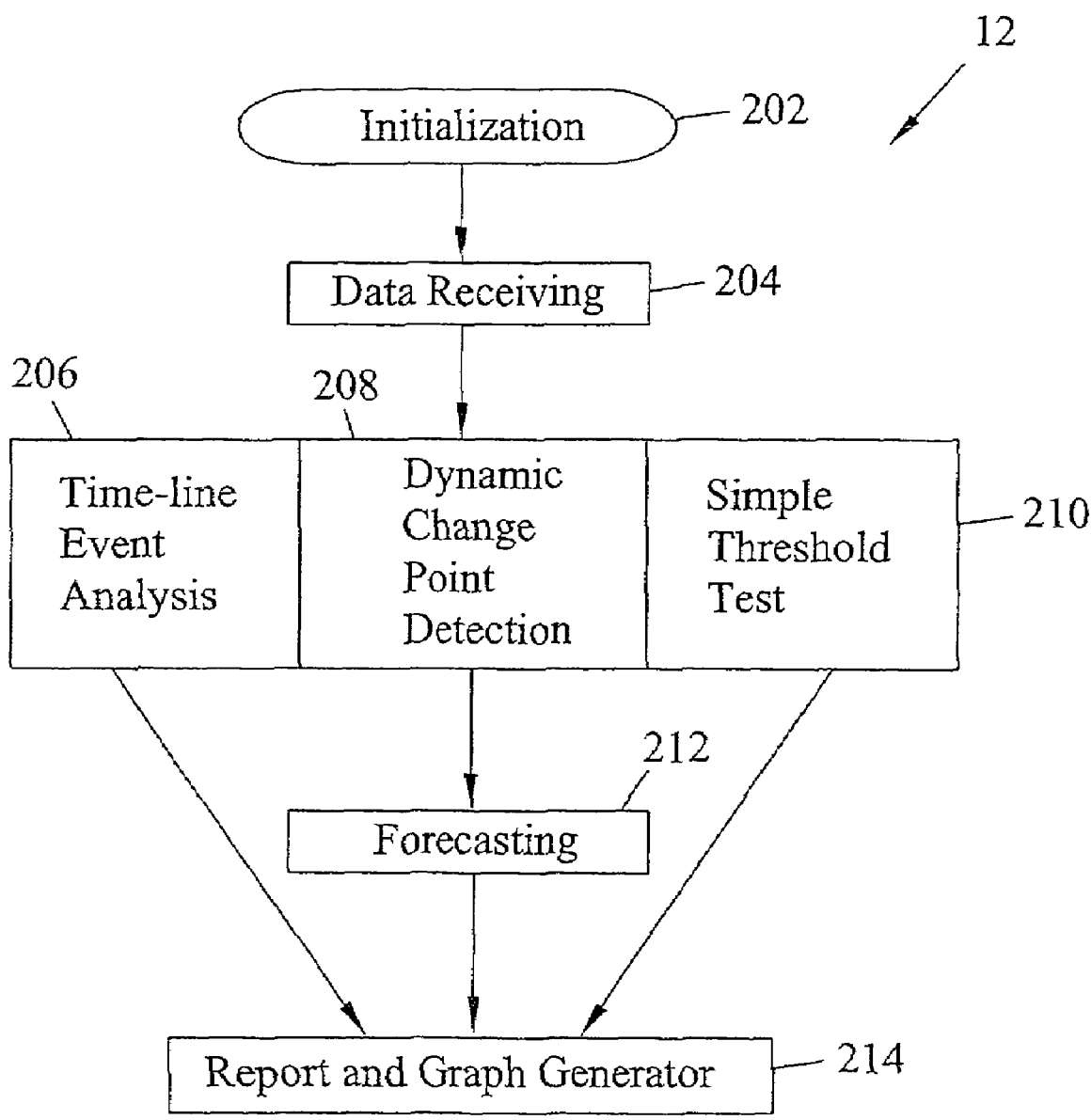
FIG. 2 is a block diagram of a patient status data processor in accordance with an exemplary embodiment.

FIG. 2 is a block diagram of an example of a patient status data processor 12. The data processor 12 may include an initialization module 202, for initializing values used in the subsequent processing of data. The data processor 12 also includes a module 204 for receiving data. As an example, the data may include medical signs and/or lab test results and/or intervention information. The data processor 12 also may include a time-line event analysis module 206, a Dynamic Change point Detection processor 208, and/or a Simple Threshold Test module 210. The data processor 12 may also include a forecasting module 212, and a module 214 for generating report(s) and/or graph(s) and/or for transmitting data to desired external devices or users.

Figure 3:
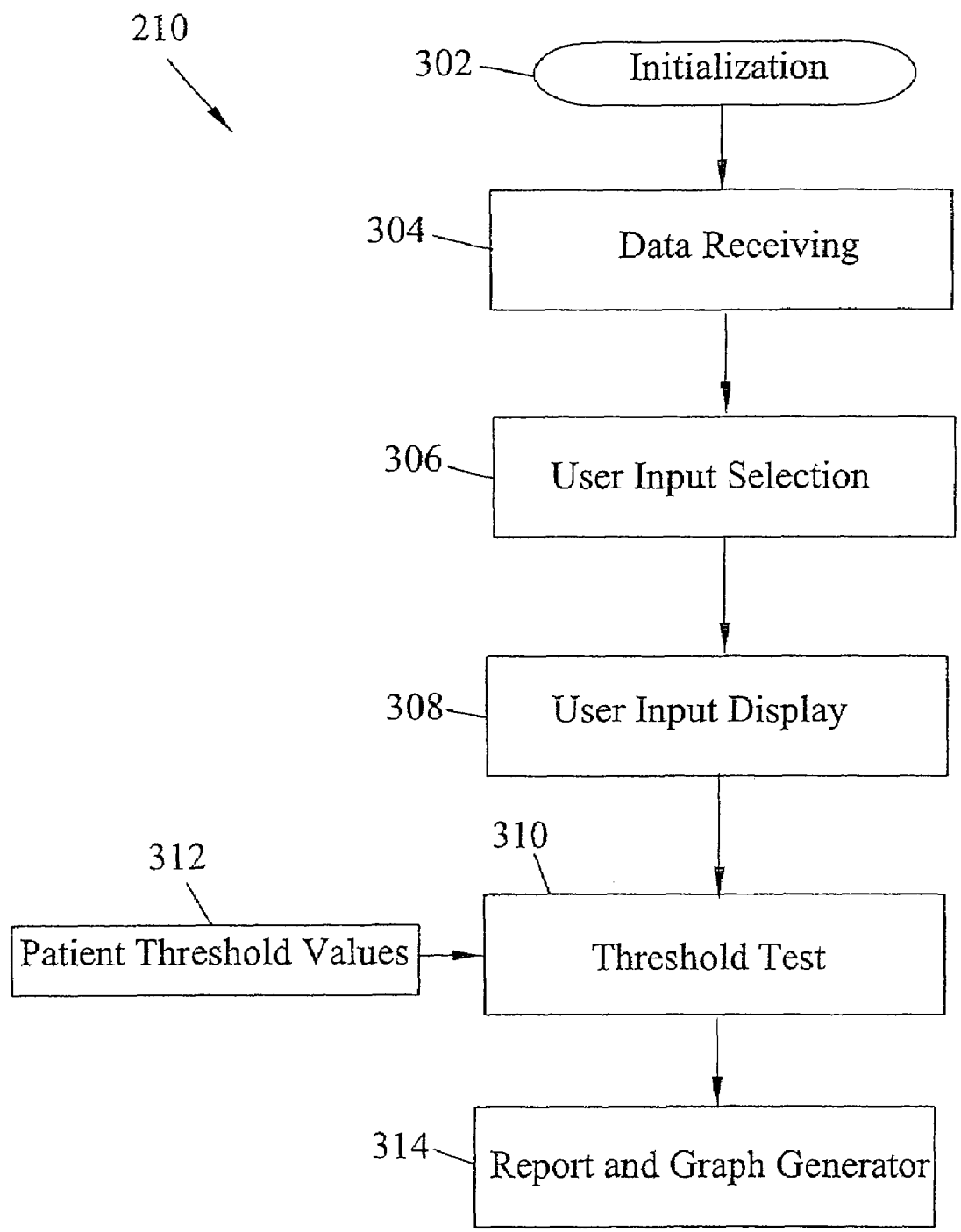
FIG. 3 is a block diagram of a simple threshold test processor in accordance with an exemplary embodiment.

FIG. 3 is a block diagram of an example of a simple threshold test processor 210. As shown in FIG. 3, the simple threshold test processor 210 may include an initialization module 302, for initializing values used for performing threshold tests. The threshold test processor 210 may also include a module 304 for receiving data. As an example, the data may include medical signs and/or lab test results and/or intervention information. The threshold test processor 210 may also include a user input selection module 306, and a user input display module 308. The threshold test processor 210 may also include a module 312 for storing patient reference values. The threshold test processor 210 also includes a threshold test module 310 for performing the threshold tests. The threshold test processor 210 may also include a module 314 for generating tabular or graphic report(s) and graph(s) and/or transmitting data to desired external devices or users.

Figure 4:
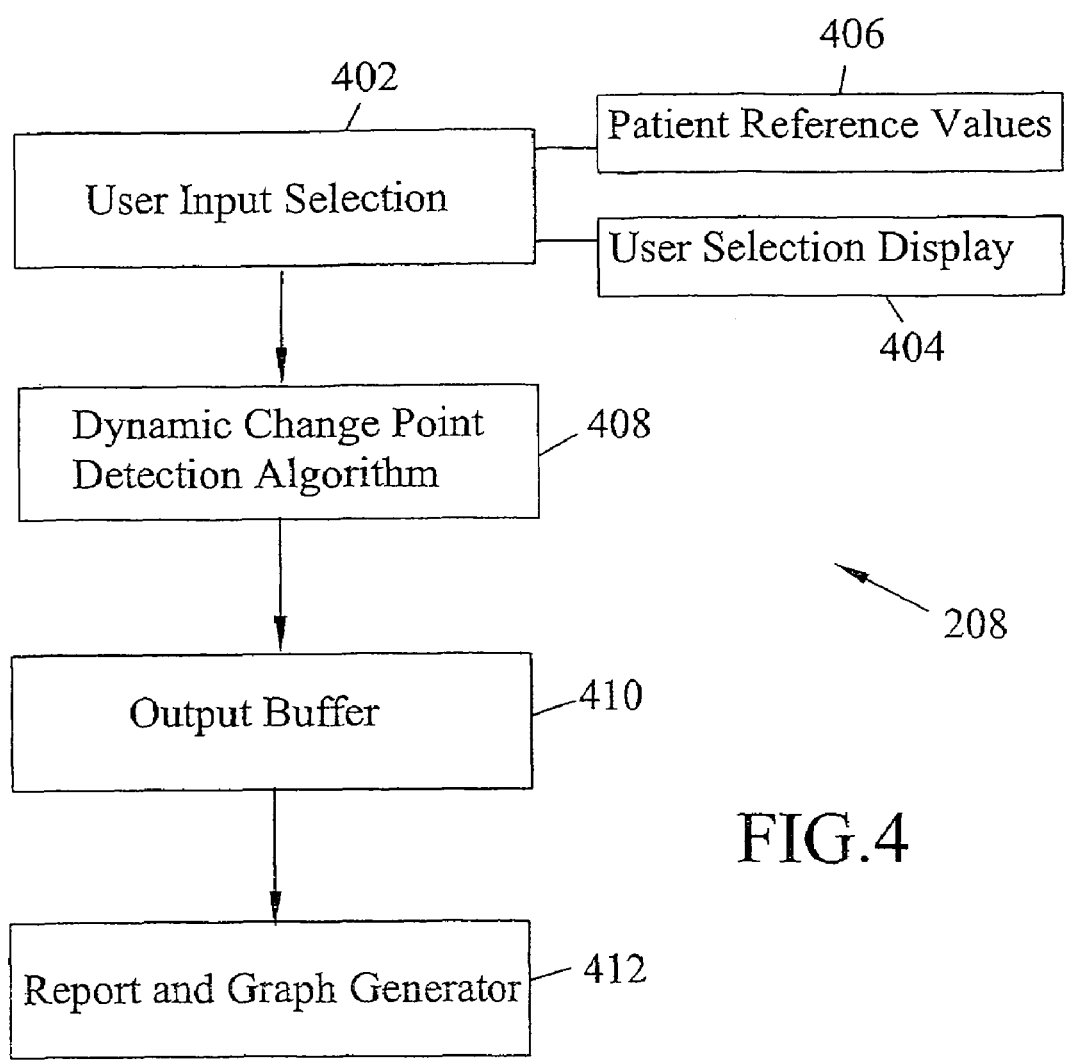
FIG. 4 is a block diagram of a Dynamic Change point Detection analysis processor in accordance with an exemplary embodiment.

FIG. 4 is a block diagram of an example of a Dynamic Change Point Detection processor 208. The Dynamic Change point Detection processor 208 may include a user input selection module 402, into which a user may input information such as a data type (eg. tissue pH, or systolic blood pressure) to be analyzed, a start date, and an end date. The Dynamic Change point Detection processor 208 may also include an output display 404 of the user selections, and a module 406 for storing data reference values (for example, patient reference values). The Dynamic Change point Detection processor 208 also includes the Dynamic Change point Detection analysis algorithm module 408, and may also include an output buffer 410 and a report and graph generator 412 for generating an output display of the results in tabular and graphic form and/or for transmitting data to an external device or user. The Dynamic Change point Detection analysis algorithm processor 208 may also include a link (not shown) to a spread sheet for viewing a subset of the data.

B. Microsensor System

Figure 13:
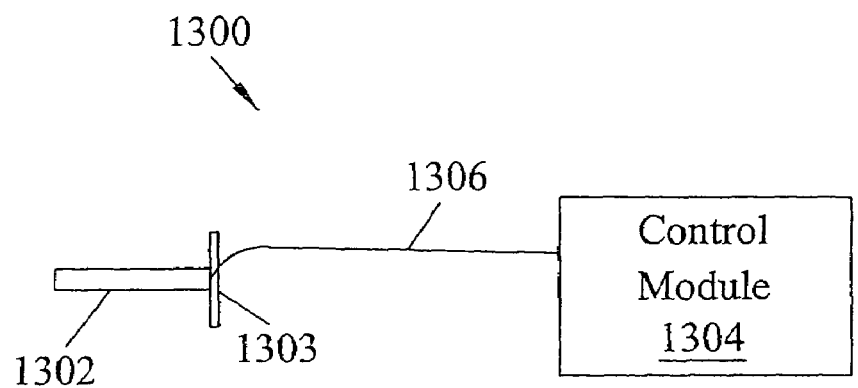
FIG. 13 is a block diagram of the hardware components and interconnections of a microsensor system in accordance with an exemplary embodiment.

FIG. 13 is a block diagram of an example of a microsensor system 1300, which in one example may be used to measure tissue pH, and which in some examples may be called a tissue pH microsensor system. The exemplary microsensor system 1300 includes a microprobe 1302, a microprobe delivery system 1303, a control module 1304, and interface 1306, which operably couple the microprobe 1302 to the control module 1304. Interface 1306 may include electrical wires, optical fiber or wireless data and/or power transmission means.

B1. Microprobe

Figure 14:
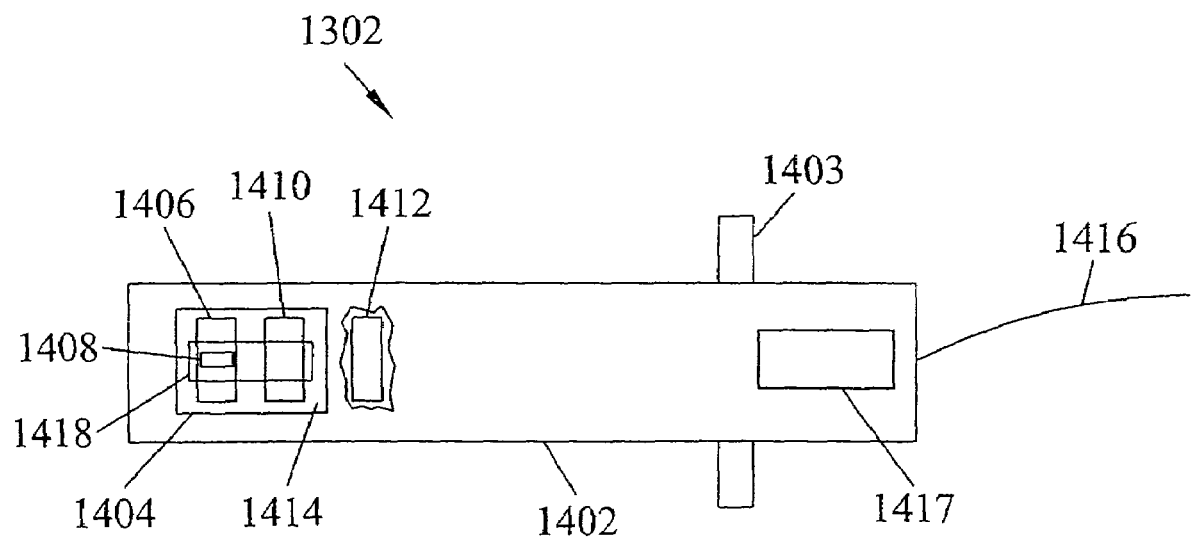
FIG. 14 is a diagram of a microprobe in accordance with an exemplary embodiment.

FIG. 14 is a diagram of the microprobe 1302 (which may be called a tissue microprobe). The microprobe 1302 must be small enough to not cause an adverse reaction in the human body, or a reaction that would interfere with obtaining accurate data. The microprobe 1302 includes a housing 1402 having an aperture 1404. The housing 1402 may have a tab 1403 for limiting the extent of incursion of the microprobe 1302 into the dermis. The microprobe 1302 also includes an ion sensitive field effect transistor (ISFET) microsensor 1406, which is attached to the housing 1402 (which may also be called an encapsulant). The ISFET 1406 has a gate 1408 located proximate the aperture 1404, as well as a source and a drain (shown and discussed with reference to FIG. 19 below). The microprobe 1302 also includes a reference electrode 1410 (which may be called a reference microelectrode), which is attached to the housing 1402 proximate the aperture 1404. As an example, the reference electrode 1410 may be made of silver (Ag), silver chloride (AgCl), Pt, or with functionally equivalent material. At least a portion of the gate 1408 and at least a portion of the reference electrode 1410 may be located within the aperture 1404. However, depending upon the exact structure of the microprobe 1302, especially in its microfabricated form, the housing 1402 and aperture 1404 may be only functionally present. Said housing 1402 may only comprise the substrate upon which all components are fabricated in sequence, such as a sapphire substrate, or an encapsulate layer, which by example might be a thin SiN4 layer, deposited or otherwise formed in regions that without the encapsulate, would not be biocompatible. As an example, the housing and the ISFET may be integrally formed in biocompatible material. As another example, the housing and the reference electrode may be integrally formed in biocompatible material. In some examples, the housing may be made of sapphire. Herein components (for example, the housing, ISFET, reference electrode and/or substrate) that are "attached" may be separate pieces that are secured together, or integrally formed components.

ISFETs have a structure that is similar to metal-oxide-semiconductor field effect transistors (MOSFETs), which are commonly used in low power microelectronics. Generally, in field effect transistors, a current flow occurs between source and drain regions, in response to modulation of channel conductivity by the gate region. In a conventional MOSFET, a voltage is applied to a metal gate to perform the modulation. In the case of an ISFET, modulation occurs by changing the surface charge on a bare gate insulator. The surface charge may change in response to the protonization-deprotonization of the gate insulator in the presence of a solution. The protonization-deprotonization is directly related to the pH of the solution.

The reference electrode 1410 may be used to complete the electrical circuit. Direct measurement of the pH of the solution may be obtained by measuring a shift in the threshold voltage (the onset of source-drain current), or by measuring the source-drain current, of the ISFET. The current flow may be coupled to a display and scaled to provide a pH readout. Thus, in some applications the ISFET may be used to measure the pH of tissue. In some examples, the microprobe could also have a blood gas sensor, which could be a second ISFET, or a single ISFET could be used for sensing blood gas rather than pH. Due to the miniaturization of the microprobe system, a plurality of sensing elements or arrays of elements could be included in the microprobe.

The microprobe 1302 may also include associated electronics circuitry 1412 attached to the housing 1402. The associated electronic circuitry 1412 need not be placed in or proximate the aperture 1404, and may be protected inside the housing 1402. In FIG. 14 a breakaway of the housing 1402 is indicated to render the associated electronics circuitry 1412 visible. As an example, the circuitry 1412 may be a temperature sensing diode or another type of sensor. In another example, the circuitry 1412 could be logic circuitry, which for example could be a logic array or a microprocessor, which could permit the microprobe 1302 to perform statistical algorithms and other logical and mathematical operations (thereby operating as a smart sensor). The ISFET 1406 and the reference electrode 1410, and also if desired the associated circuitry 1412, may be monolithically integrated. The ISFET 1406 and the reference electrode 1410, and also if desired the associated circuitry 1412, may be formed on a substrate 1414 that is attached to the housing 1402. The housing 1402 may substantially encapsulate and may hermetically seal the substrate 1414 except for a portion of the substrate 1414 within the aperture 1404, wherein at least a portion of the gate 1408 and at least a portion of the reference electrode 1410, are attached to the substrate 1414 within the aperture 1404. Thus, the housing 1402 may hermetically seal the ISFET 1406 and the reference electrode 1410, except for portions of the ISFET 1406, the reference electrode 1410 that are within the aperture 1404, to permit contact between the components in the aperture 1404 and the tissue being measured. Accordingly, the microprobe 1302 defines an exterior space that is exterior to the microprobe 1302, wherein at least a portion of the gate 1408 and at least a portion of the reference electrode 1410, are in fluid communication with the exterior space. The microprobe 1302 may be shaped, for example, as a small needle, as a cylinder, or in any other appropriate shape. The housing 1402 may be made of any suitable biocompatible material, and as an example, may comprise silicon nitride.

The microprobe 1302 also has a power/electronic interface 1416, for supplying power to the microprobe 1302, and for outputting data signals from the microprobe 1302 to the control module 1304. The power/electronic interface may be coupled to the ISFET 1406, the reference electrode 1410, and the associated circuitry 1412. In one example, the power/electronic interface 1416 is three wires (power, ground, and signal). In other embodiments, one, two, four or more wires could be used. The wires of the power/electronic 1416 interface may be long enough to connect the microprobe to the control module 1304, or may extend only a short distance from the microprobe 1302, in which case additional wires may be used to connect the microprobe to the control module 1304. Alternatively, the wires of the power/electronic interface 1416 may only reach to within the microprobe 1302, and could be attached to a socket on the microprobe 1302, which could be coupled to additional wiring to connect the microprobe 1302 to the control module 1304. Other methods could be used to couple the microprobe 1302 to the control module 1304. For example, the power/electronic interface 1416 could include a fiber-optic interface (and possibly fiber optic cable), and a fiber-optic link could be connected between the power/electronic interface 1416 and the control module 1304, for transmitting data to the control module 1304. In other embodiments, the power/electronic interface 1416 could include an electromagnetic transmitter (and possibly a receiver), for permitting untethered communications between the microprobe and the control module, and for leaving the patient untethered. For example, the electromagnetic communications could utilize free-space optical, radio-frequency, microwave, or generally any other suitable frequencies of electromagnetic waves. As an example, data signals could be wirelessly transmitted from the microprobe 1302 to the control module 1304. In examples of the microsensor system 1300 in which a plurality of microprobes 1302 are simultaneously utilized, untethered communications may be particularly useful for permitting the control module 1304 to simultaneously monitor the plurality of microprobes 1302, without having a large number of wires or fiber optic cables.

The microprobe 1302 may receive power from the control module 1304, for example, via one or more wires connected to the microprobe 1302 and the control module 1304. Alternatively, a separate power supply could be used to supply power to the microprobe 1302. Alternatively, the microprobe 1302 could include a power source 1417, which is coupled to the ISFET 1406, and which may also be coupled to the reference electrode 1410. For example, the power source 1417 could be a battery coupled to the ISFET 1406, for supplying power to the ISFET. In other examples, the power source 1417 could include a photo-voltaic electrical generator, a radioisotope-based power generator, a chemical power generator, or a kinematic power generator, coupled to the ISFET 1406. In another example, the power source 1417 could include an antenna and a capacitor, wherein the capacitor is coupled to the ISFET 1406, and the antenna is coupled to the capacitor, and wherein the capacitor is configured to store electromagnetic energy received by the antenna (for example, a pulse or series of waves), to provide power for the microprobe 1302.

The microprobe 1302 could also include a calibrant 1418 (material used for calibrating), which could be a liquid, gel, powder, solid, or gas, which is placed in contact with the gate 1408 of the ISFET 1406 and with the reference electrode 1410, for calibrating and/or testing the microprobe 1302. Alternatively, the calibrant could be included as part of the microprobe delivery system 1303 (discussed below). As an example, the calibrant 1418 could be a saline solution. The microprobe 1302 could be tested and/or calibrated, by reading the pH of the saline solution, before the microprobe 1302 is located in the tissue to be measured. If the microprobe 1302 being tested outputs erroneous data, the microprobe 1302 can be discarded, and another microprobe 1302 can be used. If the microprobe 1302 contains a plurality of sensing elements, the circuitry 1412 may employ built-in test algorithms to reconfigure the microprobe 1302 to utilize correctly functioning sensing elements following calibration.

In an alternative example of the microsensor system 1300, a plurality of microprobes 1302 are provided, and the plurality of microprobes 1302 are utilized to simultaneously gather information from different locations of the tissue being measured.

Figure 15:
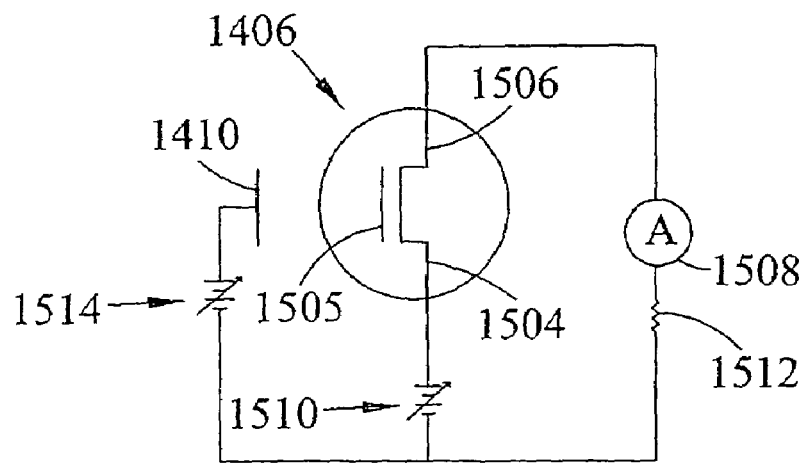
FIG. 15 is a schematic diagram showing electrical connections to components of a microprobe in accordance with an exemplary embodiment.

FIG. 15 is a schematic diagram showing an example of electrical connections to the source 1504 and drain 1506 of the ISFET 1406, and to the reference electrode 1410. The reference electrode 1410 is operably coupled to the gate insulator 1505 of ISFET 1406 via space that is exterior to the microprobe 1302. Ammeter 1508 is connected to the drain 1506, and resistor 1512 is connected in series with the ammeter 1508. Variable voltage source 1510 is connected to the source 1504, and variable voltage source 1514 is connected to the reference electrode 1410. Thus, a means 1508 for measuring the drain-source current through resistance 1512, the voltage source 1514 for biasing the gate and a voltage source 1510 for biasing the drain-source voltage complete the exemplary circuit.

B2. Microprobe Delivery System

The microsensor system 1300 may also include a microprobe delivery system 1303 (shown in FIG. 13) for delivering the microprobe 1302 to the desired tissue for assessment. For example, the microprobe delivery system 1303 could deliver the microprobe 1302 manually, pneumatically, or electrically, or using a magnetic, electromagnetic, electric, piezoelectric or electrostatic actuator, or some other type of mechanical actuator. As an example, the microprobe 1302 could be fired from a micromachined delivery system 1303 that is electrically controlled by the control module 1304. A microelectromechanical system (MEMS) may be used to implement the microprobe delivery system 1303. MEMS comprises using microelectronic processing techniques to manufacture mechanical devices. For example, a piezoelectric, electrostatic, or electromagnetic actuator, for delivering the microprobe 1302 to the desired location in the dermis, could be monolithically fabricated with the ISFET 1406 and the reference electrode 1410 (and with additional circuitry 1412 if additional circuitry 1412 is included).

Figure 16:
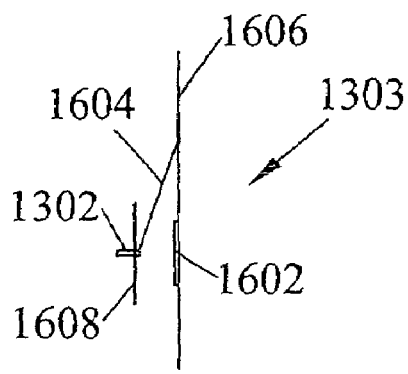
FIG. 16 is a depiction of a microprobe delivery system in accordance with an exemplary embodiment.

In the example shown in FIG. 16, the actuator 1602 of the microprobe delivery system 1303 causes a cantilever arm 1604 that the microprobe 1302 is attached to, to move from a first position near a base or pad 1606, to a second position cantilevered from the first position, in which the microprobe 1302 is inserted into the desired location in the dermis 1608. The microprobe 1302 could be designed to break off from the cantilever arm 1604 once positioned in the dermis 1608. In another example, the actuator could be configured to fire the microprobe 1302 like a projectile, into the dermis 1608.

Figure 17:
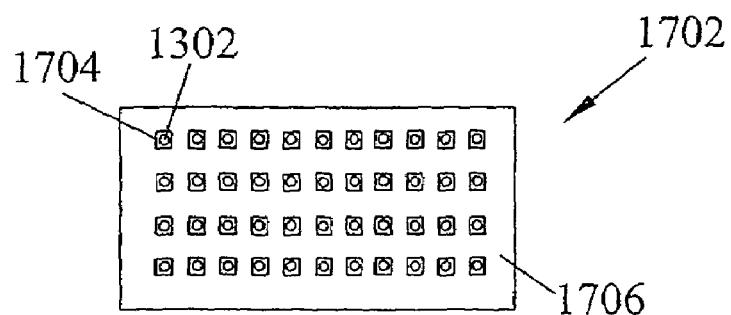
FIG. 17 is a depiction of a microprobe delivery system in accordance with an exemplary embodiment.

In an alternative example shown in FIG. 17, the microprobe delivery system 1702 has a plurality of actuators 1704, attached to a pad 1706, and is configured to deliver a plurality of microprobes 1302 into tissue, either one at a time, in groups, or simultaneously. Each microprobe 1302 may correspond with an actuator, or additional microprobes 1302 or actuators could be included. As an example, the pad 1706 could be flexible to facilitate placement against skin. Examples of methods for fabricating flexible circuitry and related microelectronic devices are found in pending U.S. patent application Ser. No. 10/313,552 (NC#79797), filed 6 Dec. 2002, titled "Flexible Display Apparatus and Method", which is incorporated herein by reference. The microprobes 1302 could be placed against the skin of a patient by placing the pad 1706 against the skin. The actuators 1704 in the microprobe delivery system 1702 could then be activated to deliver the one or more of the plurality of microprobes 1302 into the dermis of a patient, either one at a time, in groups, or simultaneously. Alternatively, rather than providing a pad 1706 having an array of actuators 1704 and microprobes 1302, a plurality of microsensors 1302 could be provided individually, and could be individually loaded into individual delivery systems, for delivery into the dermis, either one at a time, in groups, or simultaneously. The microprobe delivery system 1702 is not limited to use with pH sensors, and the microprobes 1302 discussed herein are not limited to being pH sensors. The microprobe delivery system 1702 may be used with any type of microprobe, or group or array of microprobes, for measuring, sensing, or reading data, or for delivering substances or electrical impulses, at or near the skin surface. For example microprobes could be used for sensing temperature, chemical or other biological characteristics or the skin, or could be used for applying electrical impulses. Generally, the microprobes discussed herein could be used for any of these, or additional applications.

B3. Control Module

Figure 18:
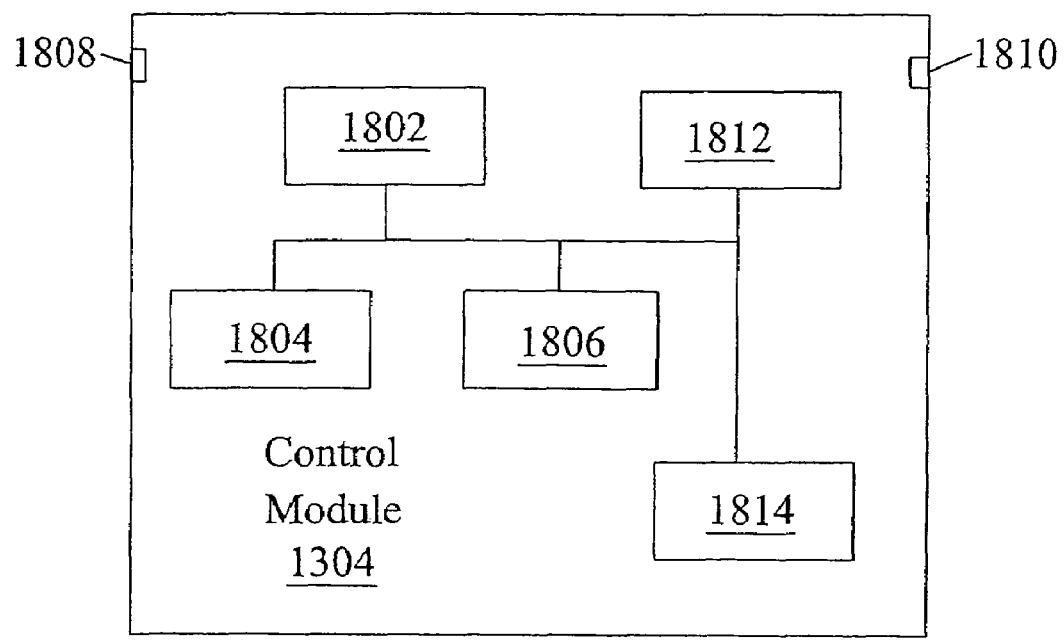
FIG. 18 is a diagram of a control module in accordance with an exemplary embodiment.

The control module 1304, shown in FIG. 18, receives, processes, and presents (or outputs) information regarding data measured by the microprobe 1302. The example of the control module shown in FIG. 18 includes a processor 1802 (which for example, may be a microprocessor), a main memory 1804 (which for example, may be RAM), a nonvolatile memory 1806 (which for example, may be an optical disc drive, a magnetic disk drive, a tape drive, or any other suitable storage device), an input 1808 (which may be an interface for receiving data from one or more microprobes 1302). The control module 1304 may also have an output 1810, which could be coupled to the display 1812 to output information to the display 1812, and which could also output information to a printer, a network, an alarm, and/or a data archiving device. In some examples, the output 1810 could output information to a patient status data processor 12 (shown in FIG. 1). The main memory 1804 and/or the nonvolatile memory 1806 may be used to store programming instructions executed by the processor 1802. The control module 1304 may also include a flat panel display 1812 for presenting information, and a user interface 1814 (which for example, may include buttons and/or knobs and/or a touchscreen, and which could include a keyboard or keypad). The control module 1304 may also have circuitry, and/or may run algorithms, for on-site calibration and/or testing, of the ISFET microsensor 1406 in the microprobe 1302. The control module 1304 may be configured to be hand held, or could be larger or smaller. In alternative examples the control module 1304 could be implemented in a personal computer, a workstation, a mainframe computer, a supercomputer or could be networked across a plurality of devices. Power for the control module 1304 may be supplied externally from the control module 1304, or from within the control module 1304, with for example, a battery, photovoltaic, chemical, radioisotope and/or kinematic electrical generator. An example of a suitable micro power device can be found in pending U.S. patent application Ser. No. 10/683,248 (NC#95867), filed 10 Oct. 2003, titled "Micro-Power Source", which is incorporated herein by reference.

The control module 1304 may be configured to output any combination of data and/or assessments. For example, the control module 1304 may present information such as tissue pH and/or temperature, as well as assessments of trends, shifts, variance, and trends in the variance, in the pH and/or temperature. The control module 1304 could further provide a shock assessment index and/or triage index, and could also present information concerning the probability of the onset of shock or death, based on appropriate algorithms. Blood flow, and/or blood gas information could also be presented by the control module 1304. The control module 1304 could also perform calculations and provide additional statistical analysis information, such as described below with regard to the patient status monitor 10, and/or described in the related applications referenced above, and/or described in U.S. Pat. No. 5,671,734, issued Sep. 30, 1997, titled "Automatic Medical Sign Monitor", which is incorporated herein by reference. In some examples, some or all of the functions of the control module 1304 could be implemented by the patient status data processor 12, described above.

B4. ISFET Structure

Figure 19:
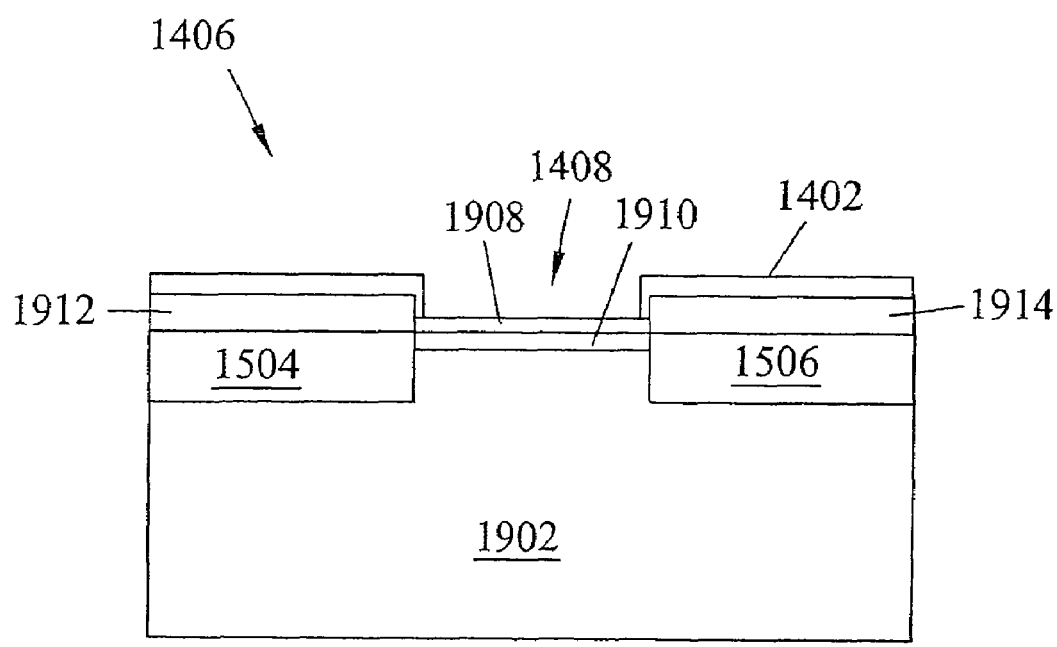
FIG. 19 is a cross sectional view of an ISFET sensor in accordance with an exemplary embodiment.

FIG. 19 is a cross sectional view of an example of the ISFET sensor 1406, which may be used in the microprobe 1302. The ISFET 1406 may be fabricated in a silicon layer 1902, which may be a portion of a bulk silicon wafer, or which may be a thin silicon layer on an insulating substrate, for example, when a silicon-on-sapphire (SOS) or silicon-on-insulator (SOI) wafer is used. Silicon-on-sapphire (SOS) and silicon-on-insulator (SOI) may permit using simpler packaging and may provide improved device performance and encapsulating advantages, in comparison to bulk silicon. Passive or active wireless communications circuitry could be readily integrated onto SOI and SOS substrates adjacent to the ISFET 1406. SOS may provide lower power, faster operation (which facilitates running real time algorithms in associated circuitry), and may be particularly beneficial for wireless communications. Sapphire has reduced toxicity and generally is more biocompatible with the human body than silicon. Exemplary methods for forming circuitry in SOS are described in pending U.S. patent application Ser. No. 10/614,426 (NC#84892), issued 7 Jul. 2003, titled "Silicon-on-Sapphire Display Apparatus and Method of Fabricating Same," which is incorporated herein by reference.

The ISFET has a source portion 1504 and a drain 1506 portion, which may be formed by incorporation of dopants into the silicon layer 1902. As an example, boron (p-type) dopants may be incorporated into n-type silicon layer 1902 by ion implantation and subsequent thermal annealing or similar techniques as practiced in the art of microelectronic fabrication, to form the source portion 1504 and the drain portion 1506. A gate insulator 1908 may be formed on the silicon layer 1902 to establish a channel portion 1910, which is defined as the predominant region of current flow when the ISFET 1406 is biased in the on state. The gate insulator 1908 may be formed in a single step or in a plurality of steps. As an example, the gate insulator 1908 may be formed by high temperature oxidation of the silicon to form stoichiometric silicon dioxide ($SiO_2$). This may be followed by the high temperature deposition of silicon nitride ($Si_3N_4$) by the pyrolysis of ammonia and dichlorosilane. Contact 1912 provides electrical contact to the source 1504, and contact 1914 provides electrical contact to the drain 1506. As an example, the contacts 1912, 1914 may be aluminum or an aluminum alloy, for example 99% Al-1% Si, or may comprise titanium-silicide or other silicides, or other materials used in the art of microelectronic fabrication. Encapsulant 1402 is formed to hermetically seal the ISFET microsensor 1406, except for the active gate region 1908 (and the reference electrode 1410) shown in FIG. 14, which are exposed to the environment. As an example, the environment could be human or animal tissue. As an example, the encapsulant 1402 may be an epoxy material that can withstand sterilization procedures required for the microprobe 1302.

B5. Microsensor System Fabrication

Figure 20A:
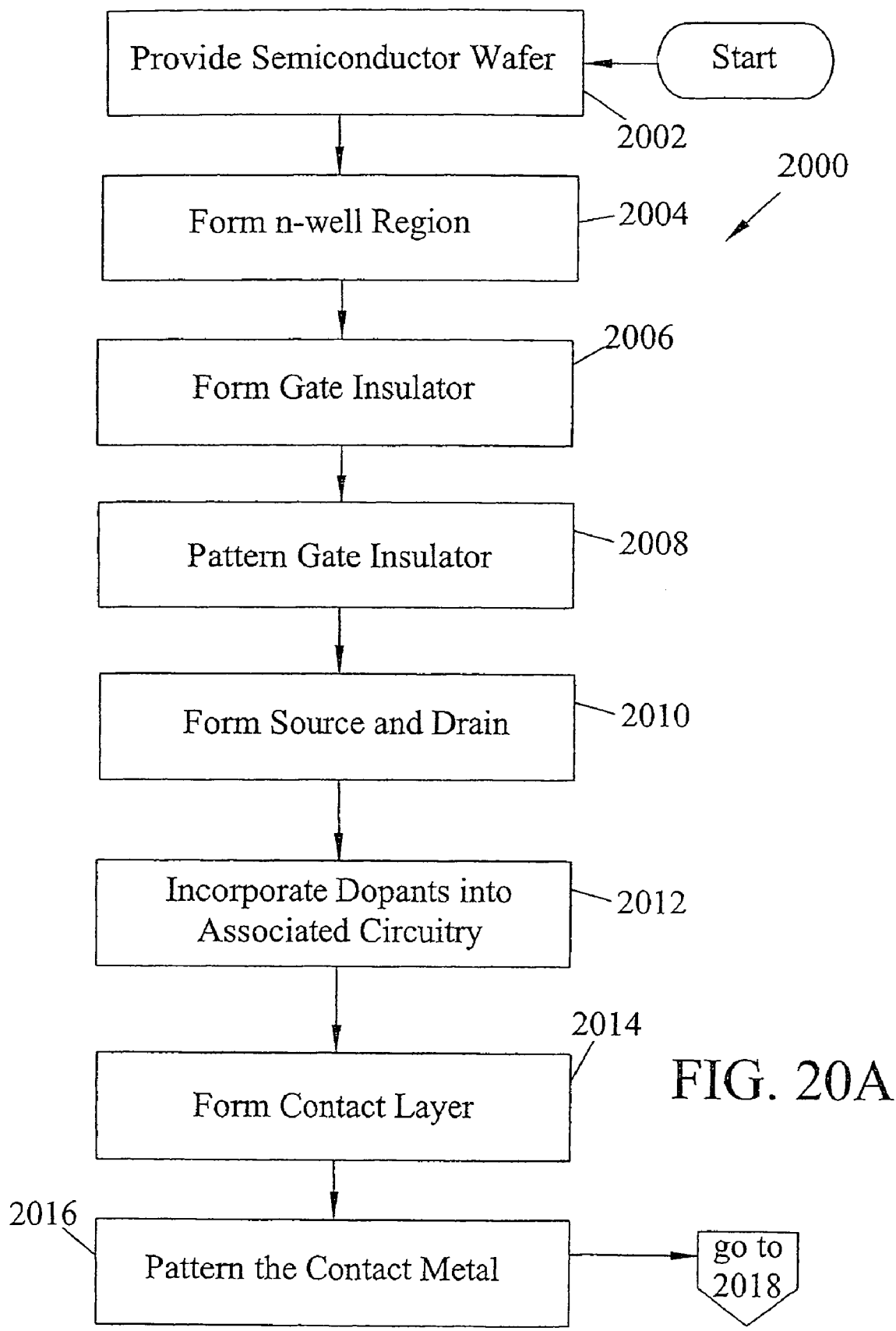
FIGS. 20A-C are a flowchart of an operational sequence for fabricating a microsensor system in accordance with an exemplary embodiment.
Figure 20B:
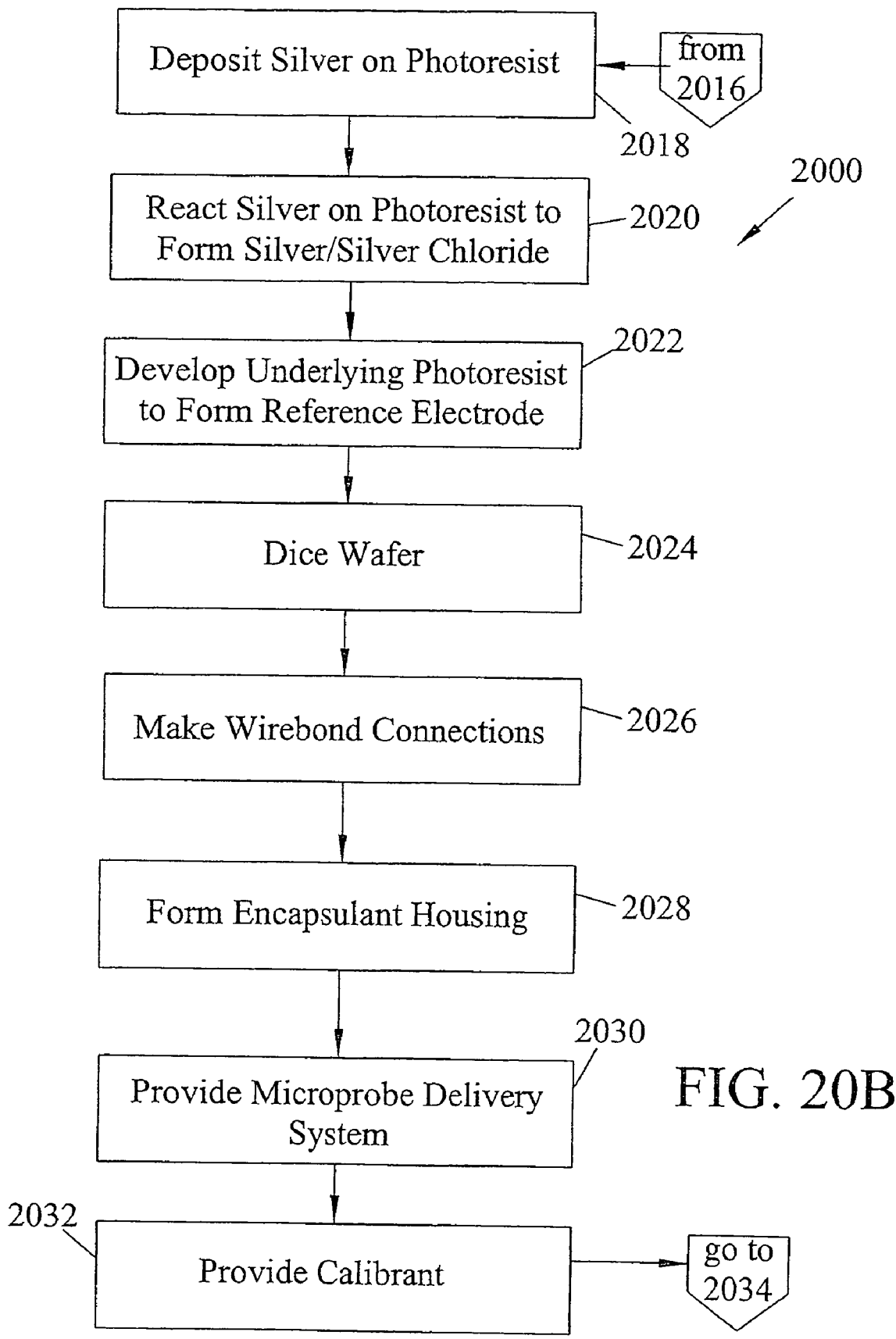
Figure 20C:
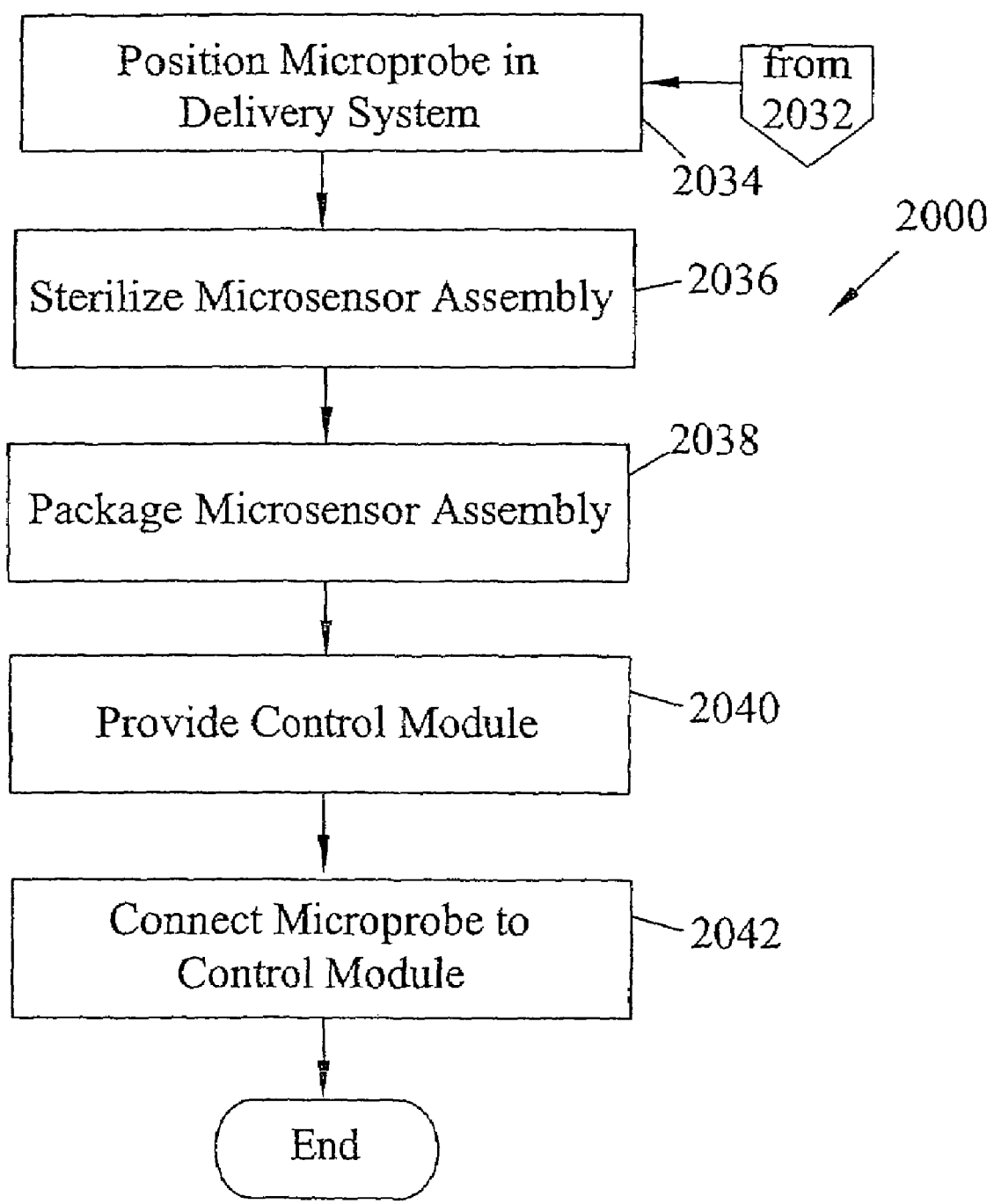

FIGS. 20A-C are a flowchart of an operational sequence 2000 for fabricating a microsensor system 1300 that includes a microprobe 1302 that has a monolithically fabricated ISFET sensor 1406, reference electrode 1410, and associated circuitry 1412, in accordance with an exemplary embodiment. In other examples of the sequence 2000, one or more of the operations may be omitted. The sequence includes operation 2002, which comprises providing a semiconductor wafer, which may for example, be bulk silicon, SOS, SOI, or other suitable material. As an example, a p-type bulk silicon wafer may be used. In operation 2004, an n-well region is formed in the semiconductor wafer, to define a semiconductor layer wherein the ISFET microsensor 1406, reference electrode 1410, and associated circuitry 1412 are fabricated. As an example, the n-well region may be formed by thermal oxidation, photolithographic patterning, and etching of the oxide. N-type dopants may be added, by using, for example, ion implantation of phosphorous followed by furnace oxidation and thermal treatment to establish the desired well depth (or drive). In the case of SOS, additional operations are employed to form a suitable semiconductor layer as described in co-pending U.S. patent application Ser. No. 10/614,426, which is previously incorporated herein.

In operation 2006, the gate insulator 1908 may be formed by a combination of growth or deposition steps as desired. As an example, a silicon layer may be thermally oxidized by heating the silicon layer in an oxygen ambient environment to form silicon dioxide. Subsequently, a silicon nitride layer may be deposited on the silicon dioxide to form the gate insulator 1908. In operation 2008, the gate insulator 1908 may be patterned, if desired, by photolithographic and etching steps known in the art of microfabrication. Patterning and etching the gate insulator 1908 provides a means for electrical contact with the source 1504 and drain 1506 regions (also called portions) that are subsequently formed, and also defines regions used by the associated circuitry (which may be included).

In operation 2010, the field, source 1504, and drain 1506 regions of the ISFET 1406 may be formed by incorporating dopants into the silicon layer, for example, by using photolithographic patterning, ion implantation, and furnace oxidation and drive. If desired, in operation 2012, dopants may be simultaneously incorporated into associated circuitry 1412 (which may be included, and as an example, may include diode circuitry). In operation 2014, a contact layer may be formed by deposition of aluminum or an aluminum alloy, using techniques known in the art, for example, by sputtering on an appropriate target. In operation 2016, the contact metal may be patterned to form contacts 1912, 1914 during photolithographic and etching steps which are known in the art of microfabrication. The reference electrode 1410 may be monolithically fabricated near the ISFET sensor 1406. As an example, the reference electrode 1410 may be fabricated using lift-off techniques known in the art as described in operations 2018, 2020, and 2022. For example, in operation 2018 the reference electrode material 1410 may be formed on a photoresist layer, by using deposition, spin-casting or related techniques as practiced in the art. As an example, the reference electrode material in operation 2018 may be silver, and operation 2018 may comprise depositing silver on the photoresist. In operation 2020, the silver may be reacted in solution to form silver chloride on the silver layer. In operation 2022, the underlying photoresist is desolved to remove the unwanted silver/silver-chloride layer, thereby producing a silver/silver-chloride reference electrode 1410 in the desired configuration, which may be described as developing the underlying photoresist to form the reference electrode 1410. Variations in device fabrication will be readily apparent to persons skilled in the art of semiconductor processing. By example, these may include such variations as to move operation 2012 to a point between operation 2004 and operation 2006 if the desired device fabrication sequence warrants it.

In some examples, a plurality of ISFETS 1406, reference electrodes 1410, and (in some embodiments) associated circuitry 1412, may be monolithically integrated on a single wafer. In operation 2024, the wafer containing the fabricated ISFET 1406, the reference electrode 1410, and associated circuitry 1412 may be diced or cleaved into individual die comprising functional units. In operation 2026, wirebond connections may be made to the ISFET 1406, reference electrode 1410, and associated circuitry 1412, using techniques known in the art. In operation 2028, the encapsulant housing 1402 may be formed around each die, respectively, to hermetically seal the die (except for the area within the aperture 1404). The aperture 1404 is formed in the encapsulant 1402 to permit contact between the tissue to be measured, and at least a portion (and typically all) of the gate 1408 of the ISFET 1406, and at least a portion (and typically all) of the reference electrode 1410, or to permit fluid communication between a fluid in the tissue, for example blood, and at least a portion of the gate 1408, and at least a portion of the reference electrode 1410.

In operation 2030, a microprobe delivery system 1303, 1702 is provided, for delivering the microprobe 1302 (or a plurality of microprobes 1302), into tissue. In operation 2032, calibrant 1418 is also provided, which may be located within the microprobe 1302, or the delivery system 1303, 1702. In operation 2034, the microprobe 1302 is positioned in the delivery system 1303 (or a plurality of microprobes 1302 are positioned in the delivery system 1702). In operation 2036, the microsensor assembly including the microprobe 1302, calibrant 1418, and delivery system 1303, 1702, is then sterilized using any suitable technique, for example, by heating in an autoclave or by utilizing high radiation doses from a radioactive source. In operation 2038, the microsensor assembly which includes the microprobe 1302, calibrant 1418, and delivery system 1303, 1702, is packaged. In operation 2040, a control module 1304 is provided, and in operation 2042, the microprobe 1302 is operably connected to the control module 1304, for example with wires 1306.

IV. Operation

In addition to the various hardware embodiments described above, a different embodiment concerns a method for monitoring data, which in some examples may be applied to measuring and/or monitoring one or more characteristics of tissue. Tissue pH is an example of a characteristic of the tissue that may be measured and/or monitored. In the examples below, "patient" status may additionally be more generally understood as the status of the system that is being monitored, which may include, for example, a manufacturing environment and the data produced from such for quality control, the stock market or other economic systems, or a population group (which may include plants, bacteria, etc.) being monitored for disease or exposure to agents injurious to their or its health.

A. Signal-Bearing Media

In the context of FIG. 1 or FIG. 13, the method for monitoring data (which in some examples may be embodied as a method for monitoring patient status, or as a method for measuring and/or monitoring a characteristic of tissue), may be implemented for example, by operating the computer to execute a sequence of machine-readable instructions, which can also be referred to as code. These instructions may reside in various types of signal-bearing media. In this respect, one embodiment concerns a programmed product, comprising a signal-bearing medium or signal-bearing media tangibly embodying a program of machine-readable instructions executable by a digital processing apparatus to perform a method for monitoring data, which in some examples may be applied to measuring/monitoring patient status and/or a characteristic of tissue.

Figure 5:
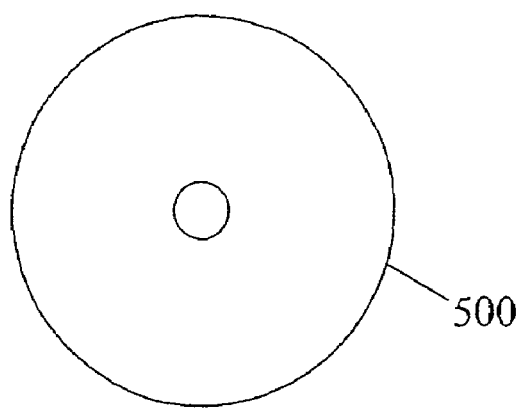
FIG. 5 shows an exemplary signal-bearing medium in accordance with an exemplary embodiment.

The signal-bearing medium may comprise, for example, the memory 28 and/or the nonvolatile storage 30 in the patient status data processor 12. Alternatively (or in addition), the signal-bearing medium may comprise, for example, the main memory 1804 and/or the nonvolatile memory 1806 in the control module 1304. Alternatively, the instructions may be embodied in a signal-bearing medium such as the optical data storage disc 500 shown in FIG. 5. The optical disc can be any type of signal bearing disc, for example, a CD-ROM, CD-R, CD-RW, WORM, DVD-R, DVD+R, DVD-RW, or DVD+RW. Whether contained in the patient status data processor 12, the control module 1304, or elsewhere, the instructions may be stored on any of a variety of machine-readable data storage mediums or media, which may include, for example, direct access storage (such as a conventional "hard drive", a RAID array, or a RAMAC), a magnetic data storage diskette (such as a floppy disk), magnetic tape, digital optical tape, RAM, ROM, EPROM, EEPROM, flash memory, magneto-optical storage, paper punch cards, or any other suitable signal-bearing media including transmission media such as digital and/or analog communications links, which may be electrical, optical, and/or wireless. As an example, the machine-readable instructions may comprise software object code, compiled from a language such as "C++".

B1. Overall Sequence of Operation of Patient Status Monitor (Which May be Used in Conjunction with Microprobe or Microprobe System)

In carrying out a method embodiment, the patient status data processor 12, shown in FIG. 1, may flag points above and below simple normal value thresholds, determine shifts in the mean, and identify outlier and burst points of, for example, a medical sign or a lab test value. The patient status data processor 12 applies the Dynamic Change point Detection (DCD) algorithm to detect a change in a patient's health state (or a change in a characteristic of tissue), to detect changes toward or away from a patient's reference value range, and to detect when no change has occurred when one should have occurred, and also employs a simple threshold test to flag values outside the patient's threshold value range. If a value is outside the patient's threshold value range or if a change in the patient's health status (or of the tissue) is indicated, then the patient status data processor 12 may display the status on a display, and/or may print a log of the patient's health status or otherwise activate an alarm status indicator or actuator. The actuator is envisioned to automatically take remedial action in response to said alarm.

The Dynamic Change point Detection algorithm is a type of trend analysis, and is used to study changes that occur in a data set over time. Using the Dynamic Change point Detection algorithm facilitates early detection of changes, which permits intervention before a problem causes irreversible damage. The problem could be a condition that slowly degrades over time or the problem could be a shift in the value of a medical sign or lab test value.

The Dynamic Change point Detection is a process that performs any one or more of the following:
1. Allows the user to exclude data points from the analysis.
2. Allows the user to change the thresholds used by one or more of the following twelve statistics. One or more of these statistics may be used in the DCD detection process. The twelve statistics are: four Shewhart test statistics, two Maximum CUSUM statistics, two Fast Initial Response CUSUM statistics, a statistical method for calculating the mean and standard deviation from the incoming data set, a statistical method for flagging and removing outliers from the mean and standard deviation estimates, a method for comparing the datapoint to a patient reference value, a method for comparing the trend direction to the patient reference value range, a method for determining a change in value is over due, and a method for determining when the mean and standard deviation should be reset and subsequently resetting the mean and standard deviation when appropriate.
3. Can set the mean and standard deviation used in the analysis from the incoming data or can use mean and standard deviation values supplied by a user or a normal value reference.
4. Can determine the mean and standard deviation from a small sample. While the Dynamic Change point Detection process is looking for 6 to 8 consistent data points, outliers are flagged and removed if their removal would not cause the standard deviation to be zero.
5. Allows the user to specify the number of consistent data points to use in calculating the mean and standard deviation.
6. Two state Markov's are initiated on the first data point. Hence the Dynamic Change point Detection process provides information on the current data point relative to the current mean and standard deviation.
7. Detects upward and downward trends, and upward and downward shifts (An upward trend is a set of datapoints whose value is increasing over time, and a downward trend is a set of datapoints whose value is decreasing over time. An upward shift occurs when the mean of the data set increases and subsequent data points occur around that mean. A downward shift occurs when the mean of the data set decreases and subsequent data points occur around that mean.),
8. Detects outliers (points two or more standard deviations from the mean),
9. Detects burst points (points three or more standard deviations from the mean),
10. Can reset the estimated mean and standard deviation if the mean in use is found to be significantly higher or lower than the incoming data.
11. Resets that change point detection statistics when shifts or trends are detected.
12. Estimates the starting and ending points of a change in the medical sign or lab test value,
13. Estimates the curve associated with the change in the medical sign or lab test value using polynomial regression,
14. Forecasts the medical sign or lab test value,
15. Calculates a confidence interval for the forecast medical sign or lab test value, and
16. Color codes detected changes. No change detected is flagged green, shifts or trends detected by the two state Markov's are flagged yellow, statistically significant shifts or trends are flagged red, outliers are flagged red, and bursts are flagged black.

Figure 6A:
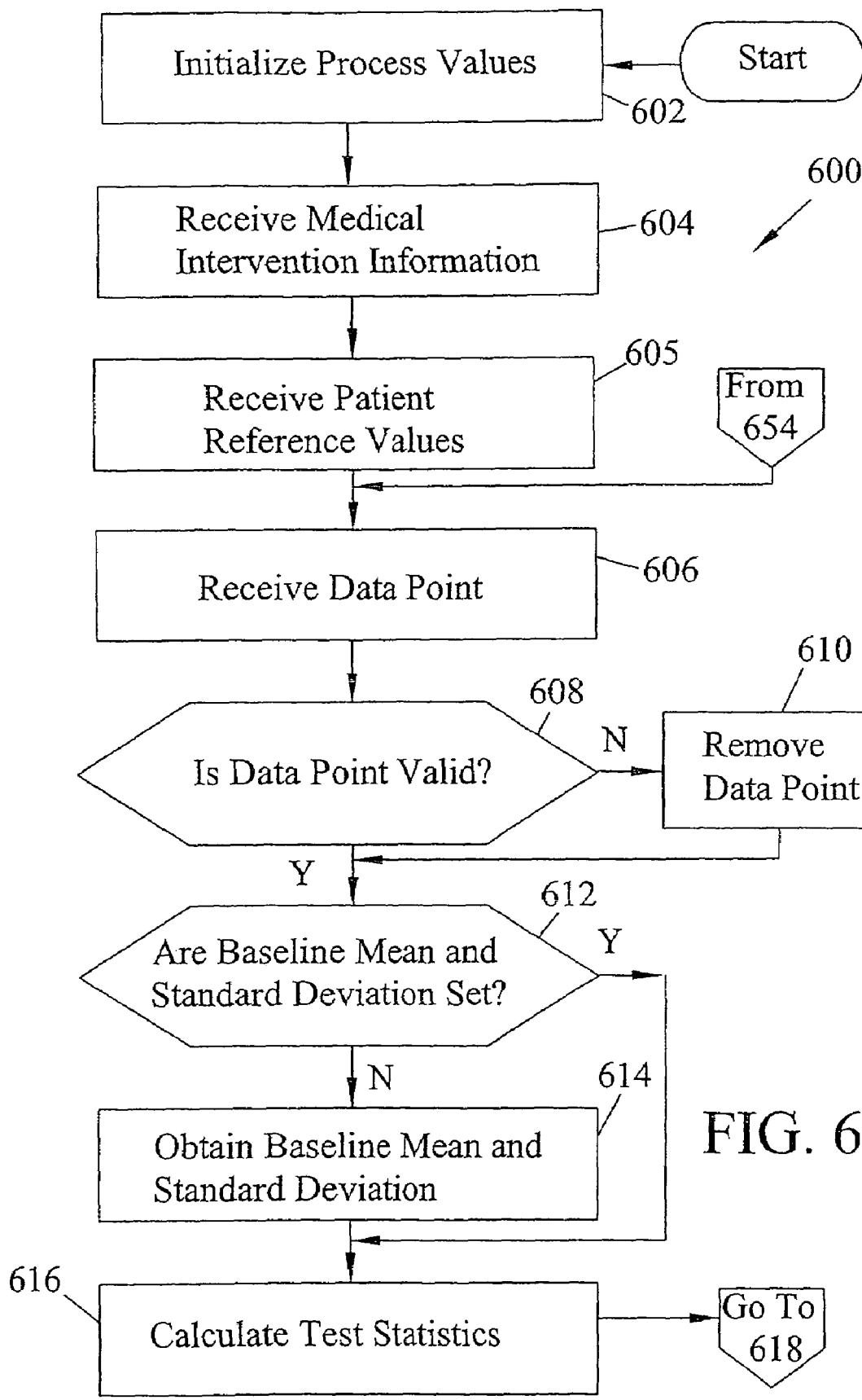
FIGS. 6A-C are a flowchart of an operational sequence for monitoring patient status in accordance with an exemplary embodiment.
Figure 6B:
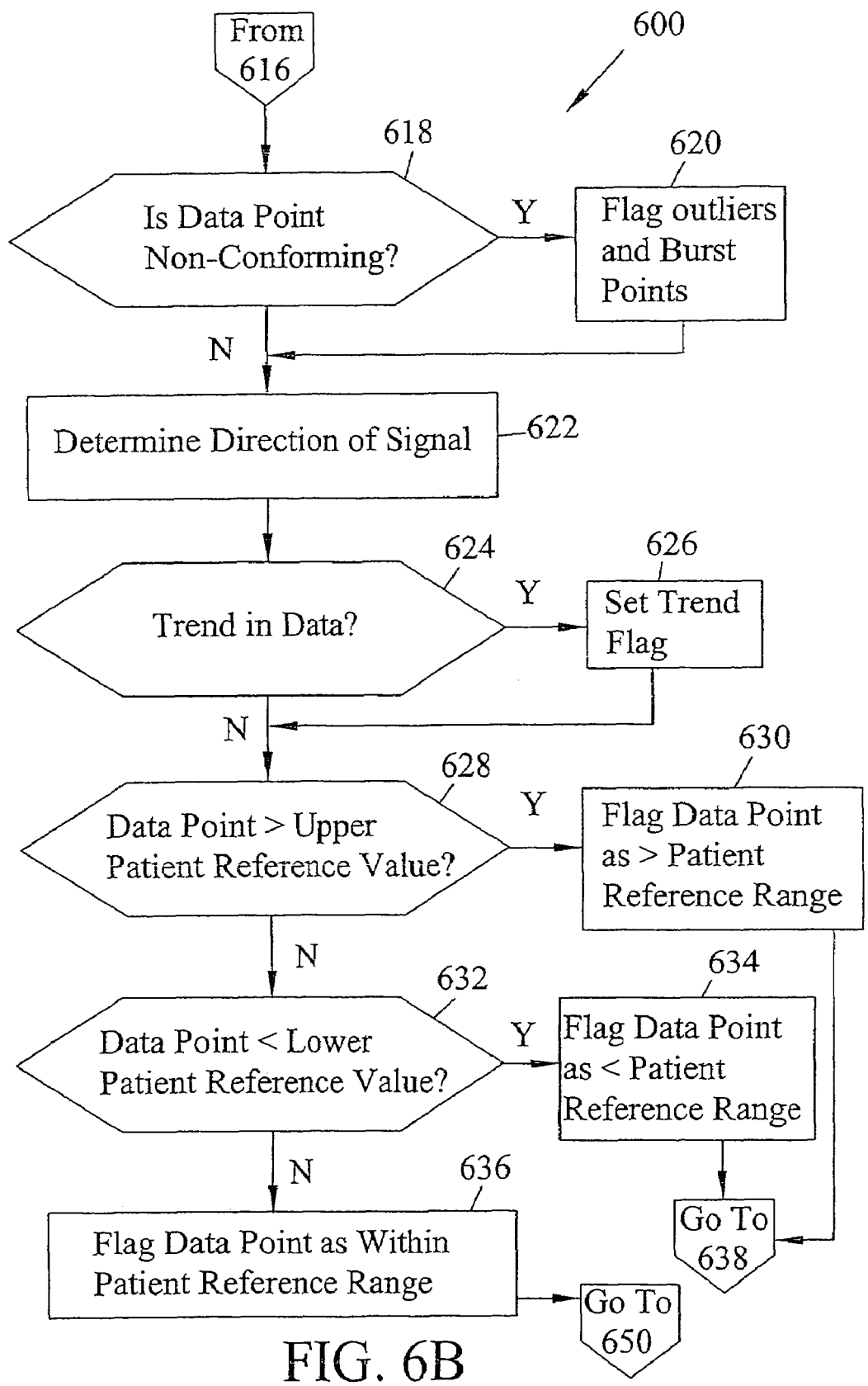
Figure 6C:
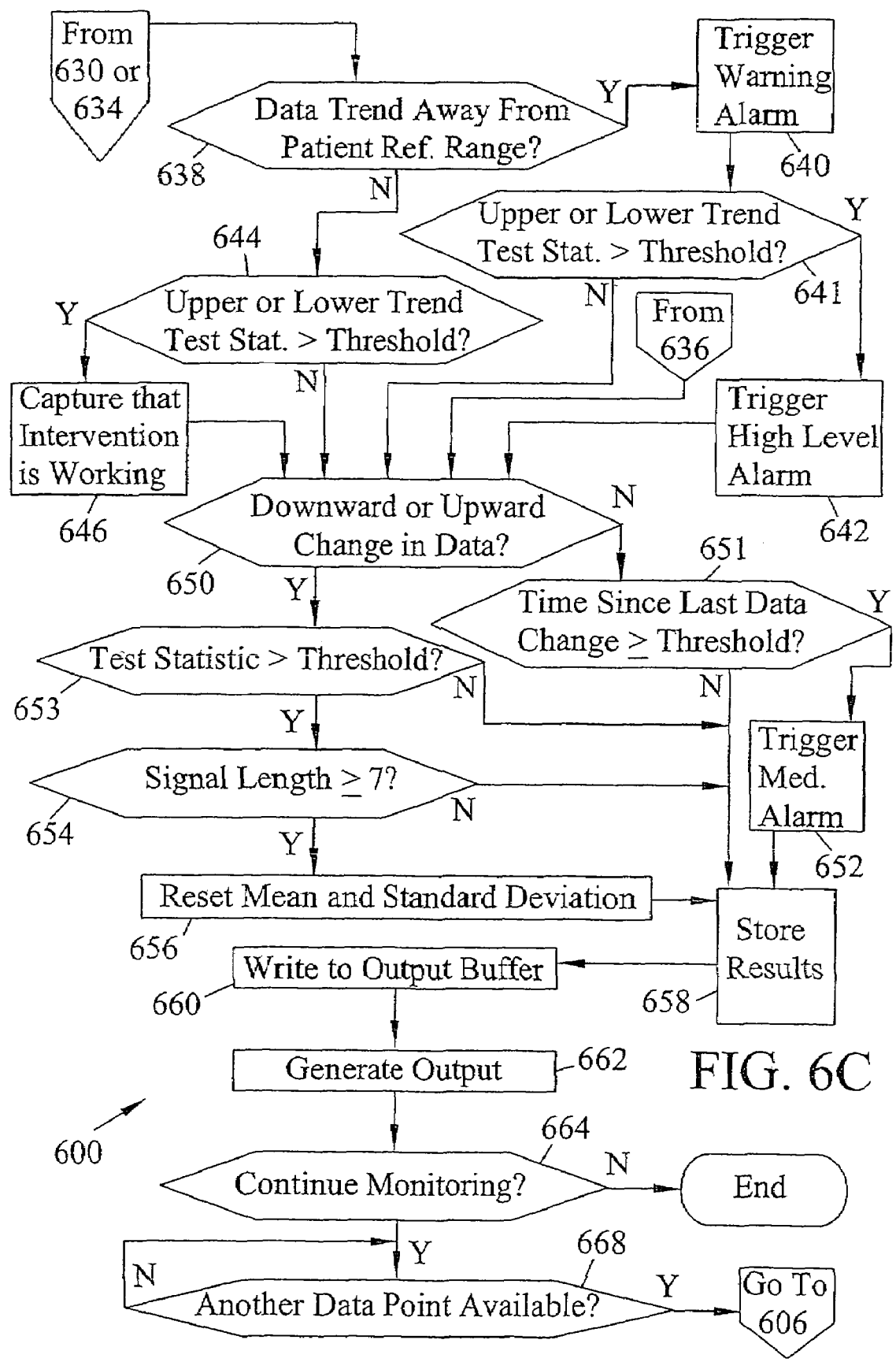

FIGS. 6A-C are a flow chart showing a sequence 600 for monitoring patient status in accordance with an example of a method embodiment. For ease of explanation, but without any intended limitation, the example of FIGS. 6A-C is described in the context of the patient status monitor 10 and the microsensor system 1300 described above. As an example, the sequence 600 may be used for detecting the onset of a disease or a change in the health status of an individual (who may also be called a patient), or for detecting the onset of shock, or for detecting whether tissue may become non-viable.

Although sequence 600 primarily seems to illustrate a method for monitoring the status of a single medical patient's status, many embodiments of the method aspect of the invention are generally applicable to monitoring data in any type of application. For example, the method for monitoring data could be used in any quality control manufacturing situation where there is a preferred reference range specification, a set of population values associated with the current manufacturing process and a number of interventions that might be done to move a process into the preferred reference range such as producing baked goods, manufacturing parts, and microchip clean room temperature and air quality particulate monitoring.

Further examples where the method may be applied include any population medical surveillance situation that includes monitoring the rates of occurrence or counts of grouping of ICD-9 codes, a single ICD-9 code, and/or signs and symptoms where these rates and counts represent the rates or counts of disease or biological exposure, injury, chemical exposure, radiological exposure, nuclear exposure, or other general health related items.

Other examples include any patient medical monitoring situation that includes monitoring signs and symptoms associated with an individual such as pulse rate, oxygenation, systolic and diastolic blood pressure, temperature, weight, tissue PH, breathing rate, EEG, chemical/horme levels, or any other signs, symptoms, or lab test values.

In other examples the method could also be applied to the stock market to watch the movement of stocks, bonds, treasury notes, money market, etc. movement toward or away from a buy or sell reference range. It could also be applied to the housing market.

The method could also be applied to the monitoring of any economic situation where there is a current value and a reference range such as the State of California's deficit current value, the interventions such as removal of the vehicle tax increase, and the preferred range of little or no deficit.

The specific example of the sequence 600 will now be discussed. The sequence 600, which may be performed by the patient status data processor 12, may include and may begin with operation 602, which comprises initializing process values.

The sequence 600 may also include operation 604, which comprises receiving medical intervention information.

The sequence 600 may also include operation 605, which comprises receiving patient reference values (which may be called patient specific tissue reference values), and patient threshold values (which may be called user input thresholds). As an example, the patient and/or tissue reference values may be determined by the patient's doctor. Upper and lower thresholds may be used in the analysis of the patient's status: Alternatively, or in addition to receiving patient reference values, normal population reference values may be inputted from a library reference table for the sign or lab test data type.

The sequence 600 may also include operation 606, which comprises receiving a data point for a data type. As an example, the data type may be tissue pH. Operation 606 may also include receiving an identifier of the data type. The data set may represent, for example, medical signs or lab data of an individual. One or more data collection devices 14, 16, 18 may provide the data that is input in operation 606. The data point may be designated $x_1$, and may be from a data set comprised of a time series of $x_1, \ldots, x_m$. In this example, "1" is the index of the first data point, and m is a positive integer that represents the number of data points that have been input and received into the process.

The sequence 600 may also include operation 608, which comprises checking validity of the data point. The validity of the data point may be based on user criteria. Data points that are determined to be invalid are removed from further consideration, in operation 610.

The patient status monitor 10 collects (or receives) a time ordered set of medical sign, and lab test data and either uses user-specified mean and standard deviation values or determines the mean, and standard deviation from the incoming data. Accordingly, the sequence 600 may also include operation 612, which comprises determining if a baseline mean and baseline standard deviation have been obtained for the data type. If a baseline mean and baseline standard deviation have not been obtained, then operation 614 is performed, which comprises obtaining a baseline mean and a baseline standard deviation. The user may specify that one or more data points not be used in the analysis, set the number of points used in calculating the mean and standard deviation, and change the threshold settings on the various statistics.

The mean and standard deviation may be calculated from the incoming data. Alternatively, the operation of obtaining a baseline mean and a baseline standard deviation may comprise using population values of the mean and standard deviation. In another alternative, the operation of obtaining a baseline mean and a baseline standard deviation may comprise using preset background values of the mean and standard deviation.

The mean and standard deviation may be derived from the currently available data points $x_1, \ldots, x_n$ that have been inputted, or may be derived from a baseline data set $x_K, \ldots, x_L$ identified during a baseline reset. "n" is defined as the current number of data points entered if the baseline mean and standard deviation have not been set, and is the last data point used to create an acceptable baseline mean and standard deviation after the mean and standard deviation are set for the first time. (The letter "m" is sometimes used instead of the letter "n".) The mean and standard deviation may be, when needed, calculated and reset a number of times. During the operation 614 of obtaining the baseline mean and standard deviation, non-conforming data points may be identified and removed from the baseline data set. A variable "r" is set equal to the number of data points removed from consideration either a priori by the user or because they are found to be non-conforming data points. When the mean and standard deviation are calculated from the incoming data, four Shewhart tests are used to remove and flag outliers in the mean and standard deviation calculations. A point that is three standard deviations or more from the mean is flagged as a burst point. A point that is between two and three standard deviations from the mean is flagged as an outlier point. Burst and outlier data points are removed from the calculations if their removal does not cause the standard deviation to be zero. The process is continued until the standard deviation is non-zero and at least seven points that meet these criteria are found. The resultant mean and standard deviation are used in the signal detection tests. An adjustment may be made in the non-conforming data point removal when the data is discrete instead of continuous.

In following description of operations performed to obtain a baseline mean and a baseline standard deviation, a first data point received in operation 606 may be referred to as the first data point, and a second data point received in operation 606 may be called a second data point. More specifically, the operation 614 of obtaining a baseline mean and baseline standard deviation may comprise:

for the first data point, setting the mean equal to the value of the first data point, and setting the standard deviation equal to zero;

for the second data point, setting the mean equal to the average of the first and second data points, and setting the standard deviation equal to zero;

for data points received after the first and second data points, calculating the mean using the formula:

$$\text{mean} = \frac{\sum_{i=1}^{m} R(x_i)}{m-r}$$

and for data points received after the first and second data points, calculating the standard deviation using the formula:

$$sd = \sqrt{\frac{\sum_{i=1}^{m}(R(x_i) - \text{mean})^2}{m-r-1}}$$

wherein $R(x_i)$ removes $x_i$ from the calculation if $$\sqrt{\frac{i-r}{i-r+1}}\left|\frac{X_i - \text{mean}}{sd}\right| \geq 2$$

or if the user has specified that $x_i$ is to be removed; and is equal to $x_i$, otherwise.

but wherein $x_i$ is not removed from the calculation if setting $R(x_i)$=remove data point i results in the standard deviation being equal to zero; (In other words, if removal of a data point will cause the standard deviation to be zero, the data point is retained.);

and wherein r is equal to the number of data points removed from the mean and standard deviation calculations; and wherein the above sequence of operations for calculating the mean and the standard deviation is repeated until the standard deviation is not equal to zero, and until at least seven conforming data points have been found.

The sequence 600 may also include operation 616, which comprises calculating test statistics. As an example, the operation of calculating test statistics may comprise applying two MAX CUSUM tests (MAXimum CUmulative SUM) to calculate an upper MAX CUSUM value and a lower MAX CUSUM value, and/or applying two FIR MAX CUSUM tests (Fast Initial Response CUmulative SUM) to calculate an upper FIR MAX CUSUM value and a lower FIR MAX CUSUM value, and/or performing four Shewhart statistical tests, and/or calculating an approximate standard score, and/or calculating signal length, and/or calculating signal amplitude or shift. The Dynamic Change point Detection processor may apply small sample versions of the statistical tests. The statistical tests are conducted on the data to detect changes in the patient's health state. If a change in a patient's sign or lab test data is indicated, then the patient's sign or lab test data health status statistics may be presented on a display.

Statistical methods used for medical monitoring may be categorized in two different categories. The first category includes statistical methods that are concerned with detecting sharp changes which are stark departures from historic levels, and that often, rapidly, return to the norm, and which are called a burst or outlier. Moving average charts and proportion charts are examples of the first type of statistical method. The second category includes statistical methods that are concerned with smaller deviations from historic levels that are sustained over an extended period of time, and which are known as a shift or trend. Linear regression and Cumulative Sums (CUSUM) are examples of the second type of statistic. Additionally, two-state Markov statistics such as the CUSUM statistic are useful for detecting shifts and trends in data, and can provide an estimate of the beginning and end of a signal. Four small-sample two-state Markov statistics may be used to detect trends and shifts in the data and to determine the beginning and end of a signal. The detection and removal of normal cyclic variation could be added to these algorithms to remove artifacts that may produce false alarms and therefore improve the detection of clinically significant events. Alternative embodiments could also include operations for forecasting the value of the data type for some time in the future using methods known to the art such as polynomial regression line fit. Additionally, alternative embodiments could include operations for reconstructing the signal present in data points (such as data points K through L discussed below).

The statistical tests will now be discussed in more detail. As mentioned above, the approximate standard score is defined as follows:

$$\hat{t}_i = (\overline{\omega})\left(\frac{X_i - \text{mean}}{sd}\right)$$

where $\overline{\omega}$ is the approximate ratio of the standard normal threshold and the t-test threshold associated with the degrees of freedom in the mean and standard deviation calculations. In an alternative embodiment the approximation is replaced with the actual ratio.

$$\overline{\omega} = \sqrt{\frac{n-r}{n-r+1}}$$

CUSUMs will now be discussed in more detail. Let $\beta$=a constant, for example 0.5, and H=the threshold used in the CUSUM statistic tests, where H is a constant chosen such that the reciprocal of the average run length equals the desired probability of false alarm.

The CUSUM upper sum is $$SH_i = \max(SH_{i-1} + \hat{t}_i - \beta, 0)$$

and the MAX CUSUM upper sum is $$SH\max_j = \max_{i=1,\ldots,j}(SH_i)$$

where $SH_0=0$.

The CUSUM lower sum is $$SH_i = \max(SH_{i-1} - t_i - \beta, 0)$$

and the MAX CUSUM lower sum is $$SLmax_j = \max_{i=1,\ldots,j}(SL_i)$$

where $SL_0=0$.

The FIR CUSUM upper sum is $$FIRSH_i = \max(FIRSH_{i-1} + t_i - \beta, 0)$$

and the FIR MAX CUSUM upper sum is $$FIRSHmax_j = \max_{i=1,\ldots,j}(FIRSH_i)$$

where $FIRSH_0 = H/2$ where H the threshold used in the CUSUM statistic tests.

The FIR CUSUM lower sum is $$FIRSL_i = \max(FIRSL_{i-1} - t_i - \beta, 0) \text{ and}$$

and the FIR MAX CUSUM lower sum is $$FIRSLmax_j = \max_{i=1,\ldots,j}(FIRSL_i)$$

where $FIRSL_0 = H/2$ where H the threshold used in the CUSUM statistic tests.

The length of the signal, the index of the signal starting point, and the data point index of the signal ending point may be estimated as follows: The upper signal length equals zero if the CUSUM upper sum is equal to zero, otherwise one is added to the upper signal length. If the MAX CUSUM upper sum is constant three times in a row, reset the CUSUM upper sum and the MAX CUSUM upper sum. The starting point in the signal is the index of the data point where the signal length is one, K, and the ending point in the signal is the index of the data point where the MAX CUSUM upper sum reached its maximum value, L. The lower signal length equals zero if the CUSUM lower sum is equal to zero, otherwise one is added to the lower signal length. If the MAX CUSUM lower sum is constant three times in a row, reset the CUSUM lower sum, and the MAX CUSUM lower sum. The starting point in the signal is the index of the data point where the signal length is one and the ending point in the signal is the index of the data point where the MAX CUSUM lower sum reached its maximum value.

The positive signal amplitude or upward shift for the ith data point is estimated as follows:

$$shift_{i,upper} = \left(\frac{SH_i}{length_{i,upper}} + \beta\right)(\varpi)(sd)$$

The negative signal amplitude or downward shift for the ith data point is estimated as follows:

$$shift_{i,lower} = \left(\frac{SH_i}{length_{i,lower}} + \beta\right)(\varpi)(sd)$$

The fast initial response (FIR) maximum cumulative sum (MAX CUSUM) algorithm and the maximum cumulative sum (MAX CUSUM) algorithm assume that the data is normally distributed around some normal value. General population normal values for each medical sign and lab test value may be contained in a normal reference. These values may be used in the calculations instead of the estimates based on the incoming data.

The mathematical derivation of the process described above is as follows. It is assumed that a set of time ordered random variables $x_1, \ldots, x_m$ of the medical sign or lab test values is normally distributed around the two known states F and G. F and G define a two state Markov process, where the first state F is associated with $x_1, \ldots, x_k$ and $x_{L+1}, \ldots, x_m$ and the second state G is associated with $x_{K+1}, \ldots, x_L$. To determine the point K where the data changes from state F to G, and the point L where the data changes from state G to F, let $$S_m = \max\left(S_{m-1} + \ln\left(\frac{g(x_m)}{f(x_m)}\right), 0\right) - \left(\frac{1}{m}\right)\min_{L \leq m} \sum_{j=L=1}^{k} \ln\left(\frac{g(x_j)}{f(x_j)}\right)$$

where L and k are chosen to maximize $S_m$. A change in Markov state from F to G occurs when $S_m$ is greater than H where H is a constant chosen such that the reciprocal of the average run length equals the desired probability of false alarm. The probability of a false alarm is approximately 0.05 for the two-state Markov process implemented. In the implemented process, a change in Markov state from G to F is assumed to have occurred when $S_{m+1}, S_{m+2}$, and $S_{m+3}$ are less than $S_m$.

The maximum value of $S_m$ may be calculated recursively according to:

$$S_j = \max\left(S_{j-1} + \ln\left(\frac{g(x_j)}{f(x_j)}\right), 0\right)$$

$$Smax_m = \max_{j=1,\ldots,m}(S_j)$$

In the FIR implementation of the maximum cumulative sum (MAX CUSUM), $S_0 = H/2$ and in the maximum cumulative sum $S_0 = 0.0$.

If $f(x)$ is distributed $N(\mu_1, \sigma^2)$ and $g(x)$ is distributed $N(\mu_2, \sigma^2)$ then if $\mu_2 \geq \mu_1$ $$SH_j = \max\left(SH_{j-1} + \frac{x_j - \mu_1}{\sigma} - \frac{\mu_2}{2\sigma}, 0\right),$$

and $$SH\max_m = \max_{j=1,\ldots m} (SH_j)$$

if $\mu_2 \leq \mu_1$ $$SL_j = \max\left(SL_{j-1} - \frac{x_j - \mu_1}{\sigma} - \frac{\mu_2}{2\sigma}, 0\right),$$

and $$SL\max_m = \max_{j=1,\ldots m} (SL_j)$$

As an example, $\mu_2/(2\sigma)$ may be set to 0.5. The FIR implementation of the MAX CUSUM may be used to determine when a perceived state change is statistically significant. The MAX CUSUM implementation may be used to estimate the number of data points belonging to the second state G.

The length of the second state may be estimated as follows: an estimate of L is the index of the maximum $S_j$ value. To estimate k the process looks backwards in time from $\hat{L}$ for the most recent $S_j$ value equal to zero. The associated index is an estimate of k. Therefore the estimated signal duration is $\hat{L}-\hat{k}$ data points.

To reconstruct the signal belonging to the second state G, a polynomial regression curve may be used to fit the data points from $\hat{k}+1$ to $\hat{L}$. Models that determine when a change in a value is non-critical, such as the change in the systolic blood pressure when the patient sits up or rolls over in bed, could be added.

Data points where the upper or lower MAX CUSUM value is greater than zero may be marked yellow, and points where the upper or lower FIR MAX CUSUM value is greater than H may be marked red (for example, on a Dynamic Change point Detection graph).

The sequence 600 may also include operation 618, which comprises determining if the data point is non-conforming, and if so, flagging the condition of the data point in operation 620 (which may comprise flagging outliers and burst points). Determining if the data point is non-conforming in operation 618, and if so, flagging the condition of the data point in operation 620, may comprise the following: Calculating the approximate standard score using the formula:

$$\hat{t}_i = (\overline{\omega})\left(\frac{X_i - \text{mean}}{sd}\right)$$

where $\overline{\omega}$ is the approximate ratio of the standard normal threshold and the t-test threshold associated with the degrees of freedom in the mean and standard deviation calculations. In an alternative embodiment the approximation is replaced with the actual ratio.

$$\overline{\omega} = \sqrt{\frac{n-r}{n-r+1}}$$

wherein n=the number of points used to estimate the mean and r is the number of data points that have been removed from the calculation;

but wherein $t_i$ is set to zero if $x_i - \text{mean} = 0$;

and wherein the data point is flagged as an outlier and is colored red on the Dynamic Change point Detection graph if $t_i$ is greater than or equal to two and is less than three;

and wherein the data point is flagged as a burst point and is colored black on the Dynamic Change point Detection graph if $t_i$ is greater than or equal to three.

When $t_i$ is greater than or equal to 2, $R(x_i)$ is set to remove the ith data point, and the associated upward or downward count is incremented.

Operations 618 and 620 may alternatively be described as follows. Four Shewhart tests may be conducted on the current data point to determine if the current data point is non-conforming and to flag its condition. Let $\delta$ and $\gamma$ be test thresholds where $\gamma > \delta$, for example, $\delta$ equals 2 and $\gamma$ equals 3. The four Shewhart non-conforming data flagging tests are as follows:

A positive outlier is declared if:

$$\sqrt{\frac{n-r}{n-r+1}}\left(\frac{X_i - \text{mean}}{sd}\right) \geq \delta$$

A positive burst is declared if:

$$\sqrt{\frac{n-r}{n-r+1}}\left(\frac{X_i - \text{mean}}{sd}\right) \geq \gamma$$

A negative outlier is declared if $$\sqrt{\frac{n-r}{n-r+1}}\left(\frac{X_i - \text{mean}}{sd}\right) \leq -\delta$$

And, a negative burst is declared if $$\sqrt{\frac{n-r}{n-r+1}}\left(\frac{X_i - \text{mean}}{sd}\right) \leq -\gamma$$

The number of data points in a major upward shift is determined by counting the number of times in a row the calculation is $\geq \delta$. The number of data points in a major downward shift is determined by counting the number of times in a row the calculation is $\leq -\delta$.

The sequence 600 may also include operation 622, which comprises determining the direction of any signal present at the data point. The operation of determining the direction of any signal present at the data point may comprise the following statistical:

If the CUSUM upper sum, $SH_i=\max(SH_{i-1}+\hat{t}_i-\beta,0)$, is greater than the CUSUM lower sum, $SL_i=\max(SL_{i-1}-\hat{t}_i-\beta,0)$ the signal is above the current baseline mean and is declared (described) to be increasing. If the CUSUM upper sum, $SH_i=\max(SH_{i-1}+\hat{t}_i-\beta,0)$, is less than the CUSUM lower sum, $SL_i=\max(SL_{i-1}-\hat{t}_i-\beta,0)$, the signal is below the current baseline mean and is declared to be decreasing. If the CUSUM upper and lower sums are equal, the signal is declared to be neither increasing nor decreasing.

The sequence 600 may also include operation 624, which comprises determining if a statistically significant positive or negative trend is occurring, and may reset all of the CUSUM and FIR CUSUM values. If $FIRSH_i \geq H$ a statistically significant positive trend is declared and if $FIRSL_i \geq H$ a statistically significant negative trend is declared.

The sequence 600 may also include operation 626, which comprises setting a flag, for example for triggering an alarm, if a statistically significant positive or negative trend is occurring in a medically undesirable direction. The alarm may be triggered regardless of whether the data is within a threshold. As an example, the alarm may be presented on a display.

The sequence 600 may also include determining if the data point is greater than an upper patient (or tissue) reference value for the data type in operation 628, and if so, flagging the data point as being above the normal range in operation 630. Similarly, the sequence 600 may also include determining if the data point is lower than a lower patient (or tissue) reference value for the data type in operation 632, and if so, flagging the data point as being below the normal range in operation 634. The sequence 600 may also include operation 636, which comprises flagging the data point as being within a normal range if the data point is not greater than the upper patient reference value and is not lower than the lower patient reference value for the data type. The sequence 600 may also include operation 638, which comprises conducting tests to determine whether there is a trend in the patient's data away from the patient reference range. The sequence 600 may also include operation 640, which comprises triggering a warning alarm if there is a trend in the patient's data away from the patient reference range. The sequence 600 may also include operation 641, which comprises determining if an upper or lower trend test statistic is greater than a threshold (H), to determine if a trend is statistically significant. If an upper or lower trend test statistic is determined to be greater than the threshold (H) in operation 641, then the sequence 600 may also include operation 642, which comprises triggering a high level alarm. The sequence 600 may also include operation 644, which also comprises determining if an upper or lower trend test statistic is greater than a threshold (H). If an upper or lower trend test statistic is determined to be greater than the threshold (H) in operation 644, indicating that movement has occurred toward the reference value range, sequence 600 may also include operation 646, which comprises capturing this statistically significant event that indicates an intervention is working.

The simple threshold test processor shown in FIG. 3 tests, flags, and color-codes patient medical sign and lab test values that are outside what is considered normal for the patient (or for the population as a whole). Selected patient sign and lab test values within a selected date range may be compared with patient threshold values. Values above and below the threshold values may be flagged in a table presentation and may also generate an alarm. Also, the values may be presented in a bar graph presentation (such as a DCD analysis graph), wherein values are presented over the time period selected, and values within the reference values are colored green, and values above or below the reference values are colored red. Black lines may also be drawn on the graph to display the upper and lower range for a sign or lab test value under review. Alternate annotations through use of symbology or color codes may also be employed by the user as desired, without limiting the scope of the teachings herein. A user may edit the patient reference values and patient threshold values (or normal value references). The color-coding system may also mark the estimated start and end of potential events, thereby providing investigative information to the user.

The sequence 600 may also include operation 650, which comprises determining if a downward or if an upward change is detected in input data. If no downward or upward change is detected in operation 650, then sequence 600 may also include operation 651, which comprises determining if no upward or downward data change has been detected for a user specified time (a no change time threshold) or longer, after an intervention has been implemented, and if so, the sequence 600 may also include operation 652, which comprises triggering a medium level alarm. The sequence 600 may also include operation 653, which comprises determining if a lower or upper test statistic is greater than a threshold (H) (for example, determining if a lower FIR MAX CUSUM or if an upper FIR MAX CUSUM is greater than H). The sequence 600 may also include operation 654, which comprises determining if the lower or upper MAX CUSUM indicates a signal $\hat{L}-\hat{k}$ having a length greater than or equal to seven. If the determinations in operations 650, 653, and 654 are all determined to be so, then the sequence 600 may also include operation 656, which comprises resetting the mean and standard deviation using data points inputted since a last time the lower or upper MAX CUSUM value was zero. In other words, if a downward or upward change is detected in the input data, and if the lower or upper FIR MAX CUSUM is greater than H, and if the lower or upper MAX CUSUM indicates a signal $\hat{L}-\hat{k}$ in length that is greater than or equal to seven, then the mean and standard deviation may optionally be reset using the data since the last time the lower or upper MAX CUSUM value was zero. The following equations may be used for resetting the mean and standard deviation in operation 656:

$$\text{mean} = \frac{\sum_{i=\hat{k}+1}^{\hat{L}} R(X_i)}{\hat{L}-\hat{k}-r},$$

and $$sd = \sqrt{\frac{\sum_{i=\hat{k}+1}^{\hat{L}} (R(X_i)-\text{mean})^2}{\hat{L}-\hat{k}-r-1}}$$

wherein $R(x_i)$ removes $x_i$ from the calculation if $$\sqrt{\frac{\hat{L}-\hat{k}-r}{\hat{L}-\hat{k}-r+1}} \left| \frac{X_i - \text{mean}}{sd} \right| \geq 2$$

or if the user has specified that $x_i$ is to be removed; and is equal to $x_i$, otherwise.

Generally, there are four potential reset conditions that may be implemented. Conditions applied are dependent on the initialization by the end-user.

Condition 1: If the signal is statistically significant, and contains enough data points to try a baseline reset, and the signal change direction is toward the normal range, then the baseline should be reset and the information that the mean value has moved toward the normal range is captured. Condition 1 may occur because the initial data points used in calculating the mean and standard deviation contained a signal and was not noise only data. Condition 1 may also indicate an improvement in the patient's status. For example a patient's drop in mean diastolic value from 105 to 100, which is still high, is an improved mean. If this is the case, it would be desirable to monitor for a continued decreased in diastolic value.

Condition 2: If the signal is statistically significant, and contains enough data points to try a baseline reset, and the signal change direction is increasing and farther away from the normal range, then the baseline should be reset and the information that the mean value has increased and is farther away from the normal range is captured.

Condition 3: If the signal is statistically significant, and contains enough data points to try a baseline reset, and the signal change direction is decreasing and farther away from the normal range, then the baseline should be reset and the information that the mean value has decreased and moved farther away from the normal range is captured.

Condition 4: If the signal is statistically significant, and contains enough data points to try a baseline reset, and the signal change is still within the normal range, then the baseline should be reset and the information that the mean value has moved within the normal range is captured.

In alternative embodiments an additional set of four conditions could be used based on user input patient reference thresholds for the sign or lab test values.

The sequence 600 may also include operation 658, which comprises storing the results for an i-window length of data points. The processing window length may be set to a constant, for example 30, during the initialization operation 602. Additionally, the sequence 600 may include operation 660, which comprises writing data to an output buffer.

The sequence 600 may also include operation 662, which comprises generating a data output signal that represents a statistically significant change in the patient (or tissue) status. The operation of generating a data output signal may comprise outputting results, for an i-window length of data points that includes the data point, wherein the outputted results may include any of the following, all of the following, or any combination of the following: (1) a time-line event report that includes at least some of the medical intervention information, (2) a Dynamic Change point Detection graph, and (3) a time sequenced table (also called a trend analysis report) containing statistical information. The time sequenced table includes at least some information contained in the time-line display, the threshold test graph, and the Dynamic Change point Detection graph. The time-line event report, the Dynamic Change point Detection graph, and the time sequenced table containing statistical information, may be displayed simultaneously on a single display. The outputting operation may further comprise outputting a threshold test graph. The outputted results may be displayed on one or more display devices such as a computer display screen or other type of video monitor (including a web browser), may be printed on a printer, stored in a data archive, copied to a computer program (such as a word processor or presentation program), and/or emailed.

Figure 7:
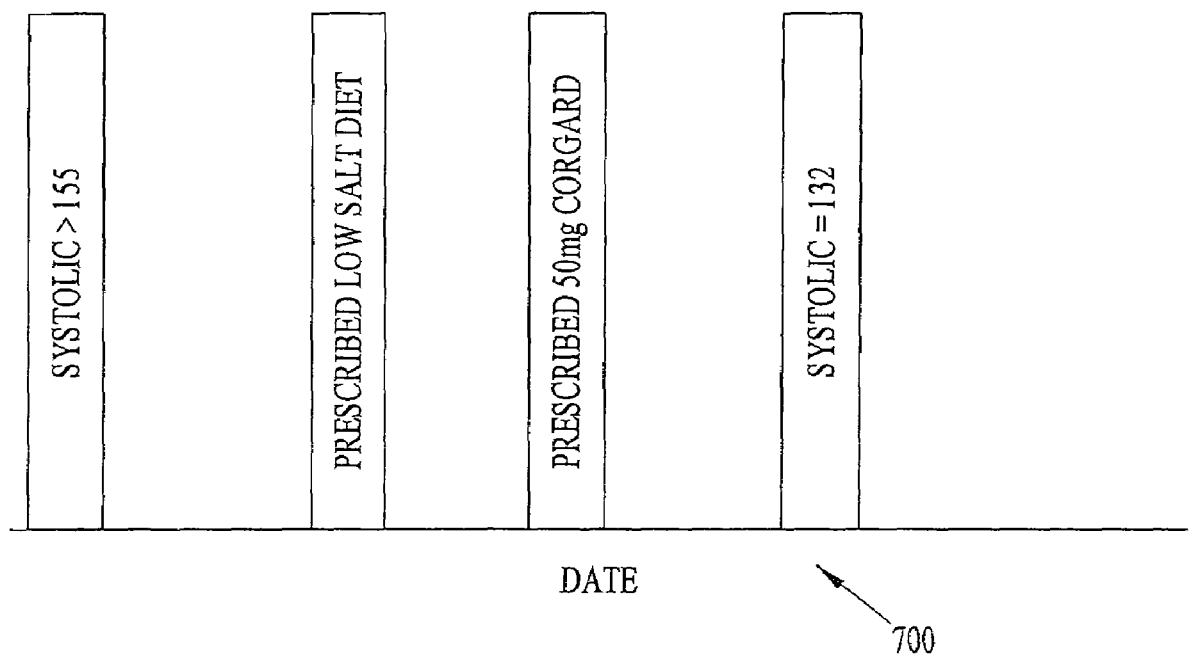
FIG. 7 is a time-line event graph in accordance with an exemplary embodiment.

FIG. 7 shows an example of a time-line event graph (or report) 700. The time line event analysis (time line graph) is a one dimensional x-axis graph that includes information gathered by the sign sensor 14, the lab test sensor 16, and/or the intervention data collector 18. Time may be indicated in days, and medical interventions such as changes in medication or treatment plan, along with medical signs and/or lab test results, may be shown in text windows along the x-axis. The user may be permitted to add additional comments to these text windows. The text shown on the time line may be limited in length. A further explanatory text field of information for each item may be made available through a hyperlink. The text associated with the time line graph may be added to the patient's treatment record. The time-line graph may be presented simultaneously with a color coded Dynamic Change point Detection graph, thereby providing an attending medical physician an easy to read record of the patient's current and past status, along with what corrective actions have been taken. Using the time line graph in conjunction with the Dynamic Change point Detection graph is particularly useful, because medical data monitoring entails more than merely determining when the medical data change is statistically significant, and it requires understanding the clinical significance of the medical data changes.

Figure 8:
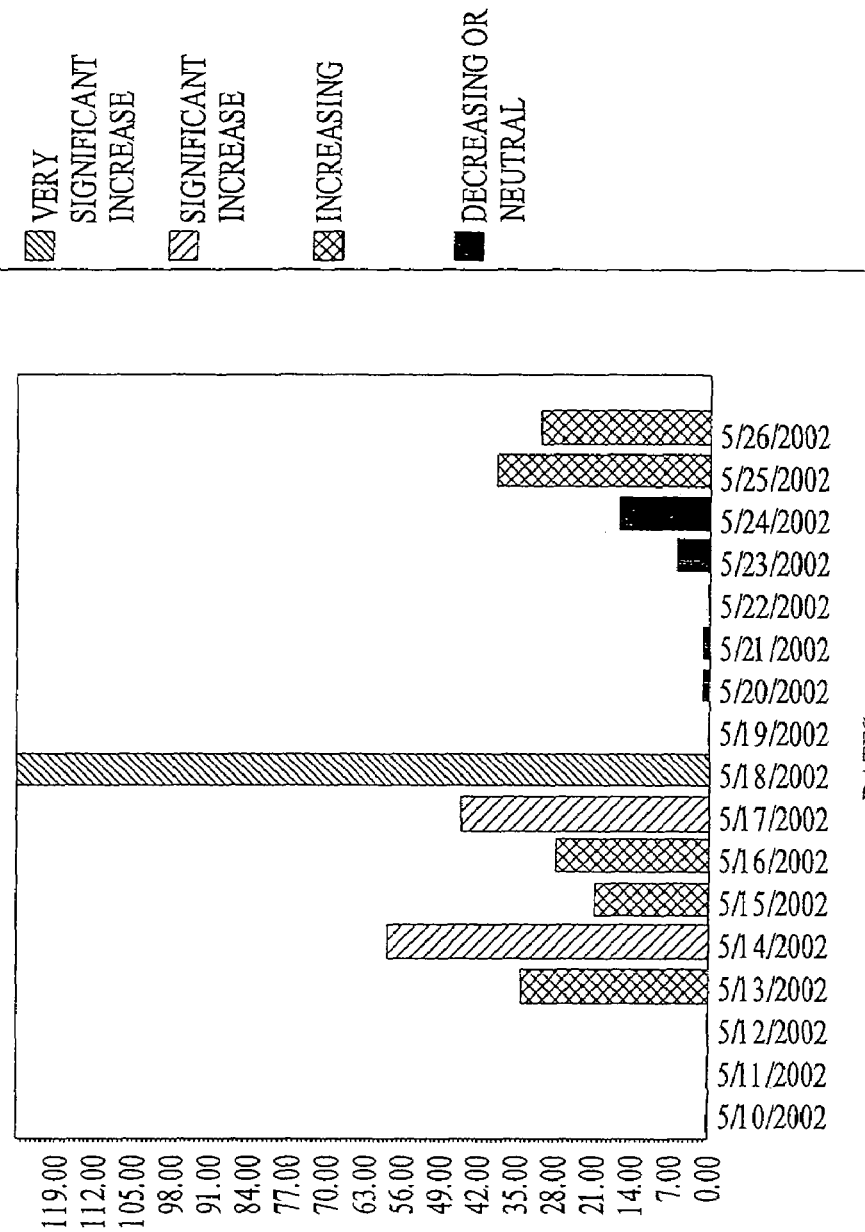
FIG. 8 is a Dynamic Change point Detection graph in accordance with an exemplary embodiment.

FIG. 8 shows an example of a Dynamic Change point Detection graph 800. The Dynamic Change point Detection graph (data trend analysis graph) displays information that includes the results from the DCD algorithm. The graph may indicate a sign or lab test value or counts or rates of occurrence of an event on a Y-axis and days on a X-axis. In one embodiment, the graph is color-coded. For example, a black bar may indicate data points that are three or more standard deviations from the mean. A red bar may indicate data points that are between two and three standard deviations from the mean, or a statistically significant trend or shift. A yellow bar may indicate an increasing trend less than two standard deviations from the mean. A green bar may indicate that there is either no trend or a decreasing trend.

FIG. 9 shows an example of a data analysis report 900. The table (trend analysis report) permits looking at information regarding actual data points in table format. The table may contain a number of columns. A date column may specify the date a case occurred. Another column may indicate a selected sign or lab test value or count or rate of an event occurring that day (daily incidence). Another column may include the calculated mean, and another column may include the standard deviation. A trend direction column may be included to indicate whether the value, counts, or rates are increasing or decreasing relative to the mean. A trend length column may be included to indicate the number of data points/days that are included in the current upward or downward trend/shift data set. A statistically significant event column may be included to indicate what type of statistical event has occurred. Possible events may include, for example, positive burst, negative burst, positive outlier, negative outlier, positive trend/shift or negative trend/shift mean.

FIG. 10 shows another example of a data analysis report 1000. The table (FIR SHEWHART CUSUM report) permits looking at information regarding actual data points in table format. The table may contain a number of columns. A date column may specify the date a case occurred. Another column may indicate a selected sign or lab test value or count or rate of an event occurring that day (daily incidence). Another column may include the calculated mean, and another column may include the standard deviation. Another set of columns may present the number Shewhart test statistic, Z, the lower maximum CUSUM test statistic, SL(I) and the upper maxium CUSUM test statistic, SH(I). A trend direction column may be included to indicate whether the counts are increasing or decreasing relative to the mean. A statistically significant event column may be included to indicate what type of statistical event has occurred. A trend or signal length column may be included to indicate the number of data points/days that are included in the current upward or downward trend/shift data set. Possible events may include, for example, positive burst, negative burst, positive outlier, negative outlier, positive trend/shift or negative trend/shift mean. These events may also include information on the direction of a trend relative to the patient reference value range. In addition, this information may also specify the data points, if any, that are above or below the patient's threshold range, and may indicate if there has been no change within a user specified length of time after an intervention. Also, columns containing the calculated shift from the normal value, smoothed value, and upper and lower confidence intervals could be included. In addition, the patient reference values and patient threshold values may be displayed.

Figure 11:
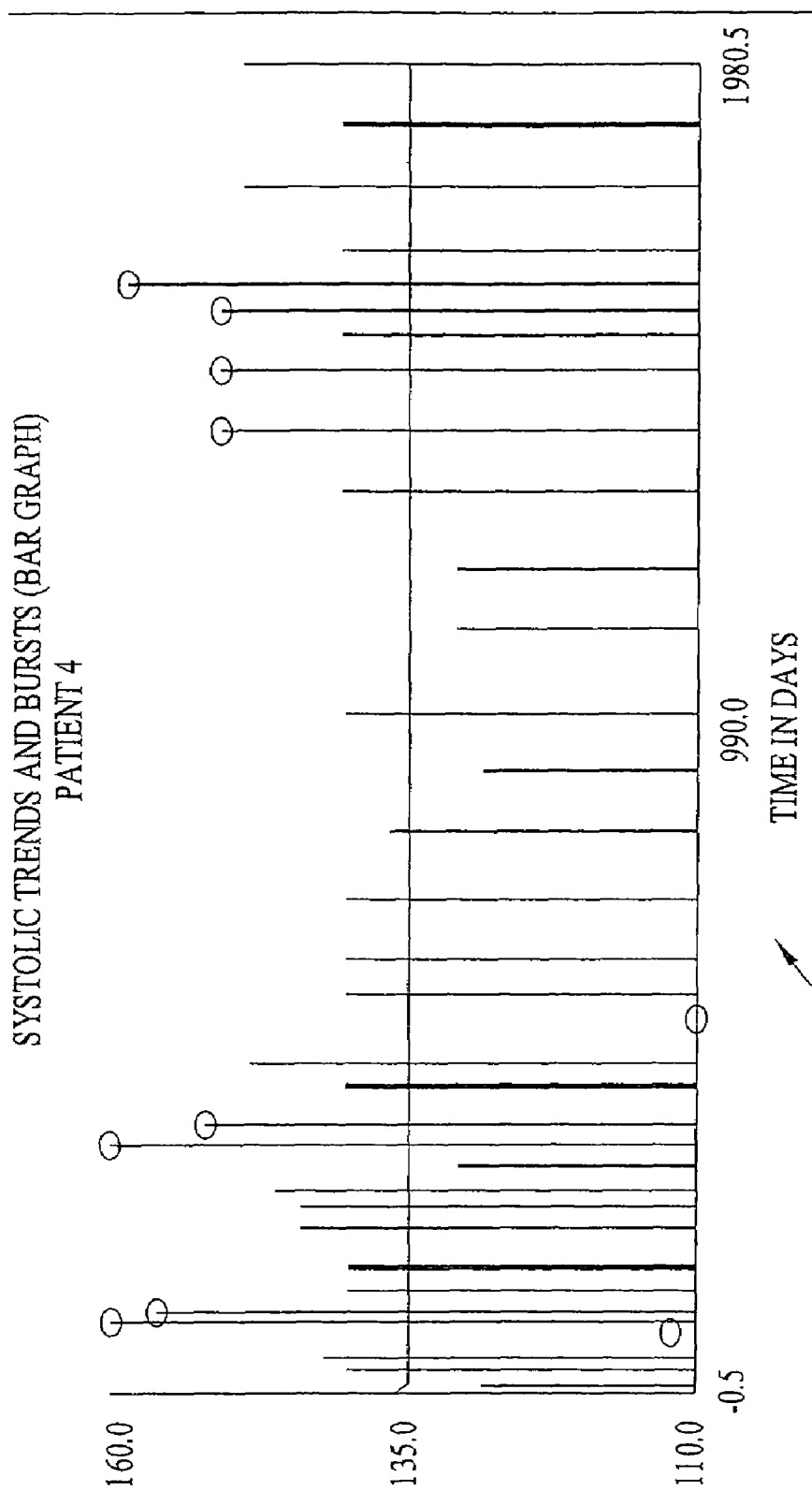
FIG. 11 is a Dynamic Change point Detection graph displaying unequal time interval data in accordance with an exemplary embodiment.

FIG. 11 shows an example of a Dynamic Change point Detection graph 1100. The Dynamic Change point Detection graph (data trend analysis graph) displays information that includes the results from the DCD algorithm. The graph may indicate a sign or lab test value or counts or rates of occurrence of an event on a Y-axis and days on a X-axis. In one embodiment, the graph is color-coded. For example, a white bar may indicate data points that are three or more standard deviations from the mean. A red bar may indicate data points that are between two and three standard deviations from the mean, or a statistically significant trend or shift. A yellow bar may indicate an increasing trend less that is than two standard deviations from the mean. A green bar may indicate that there is either no trend or a decreasing trend. Data used in the process, as shown, may be collected (or received) at uneven time intervals.

Figure 12:
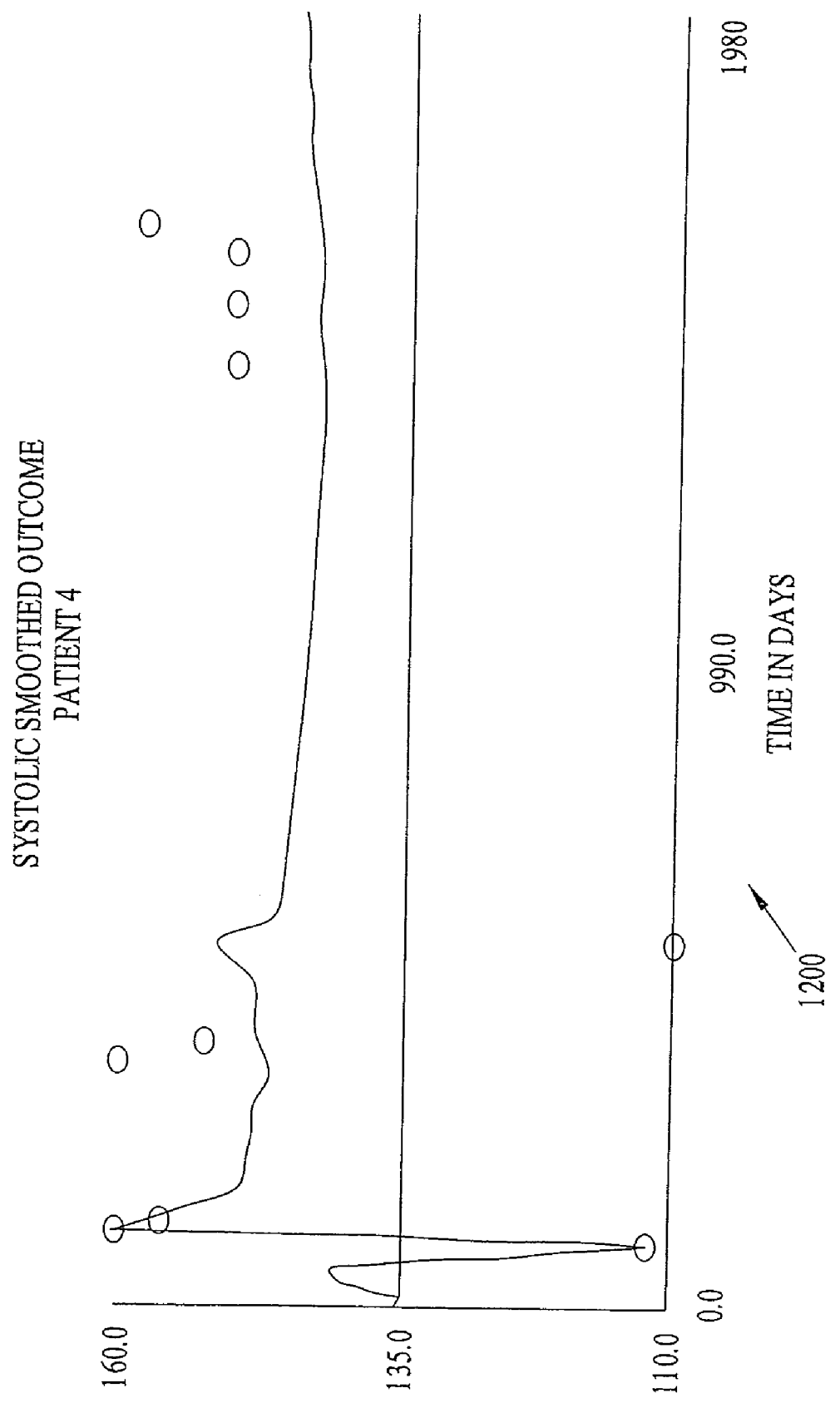
FIG. 12 is a Dynamic Change point Detection graph displaying smoothed output and outliers in accordance with an exemplary embodiment.

FIG. 12 shows another example of a Dynamic Change point Detection graph 1200. The Dynamic Change point Detection graph (data trend analysis graph) displays information that includes the results from the DCD algorithm. The graph may be of the smoothed output values and may also display data points associated with statistically significant events and/or alarms. The graph may indicate a sign or lab test value or counts or rates of occurrence of an event on a Y-axis and days on a X-axis. In one embodiment, the graph is color-coded. For example, a white circle may indicate data points that are three or more standard deviations from the mean. A red circle may indicate data points that are between two and three standard deviations from the mean, or a statistically significant trend or shift. Data used in the process, as shown, may be collected (or received) at uneven time intervals.

A simple threshold test graph may also be outputted, and may be presented with some or all of the other outputted information. Also, the results for one or more days may be downloaded to a spreadsheet for further analysis.

Referring again to FIG. 6C, sequence 600 may also include operation 664, which comprises determining if the patient status monitoring is to continue or end. If the patient status monitoring is to continue, sequence 600 may also include operation 668, which comprises determining whether another data point is available for processing, or if the process must wait (and perhaps enter a sleep mode) until another data point is available. When another data point is available, the sequence 600 repeats beginning at operation 606.

One exemplary embodiment may be described as a method for monitoring patient status, comprising the following operations:

a) receiving and storing $i^{th}$ data in an array, where i is an index;

b) determining a mean and a standard deviation from consistent data for use with said $i^{th}$ data, and identifying and flagging non-conforming data from said array so that said consistent data exclude flagged non-conforming data if: i) no a prior mean and standard deviation are available, ii) if there are less than C consistent data stored in said array, iii) if a prior determined standard deviation equals zero, or iv) if a mean and standard deviation reset are required and there is at least C data in a subset of said array selected for use in said mean and standard deviation reset, where C is a positive integer;

c) determining test statistics from said $i^{th}$ data and said mean and standard deviation determined in said step (b), wherein said test statistics include a signal length;

d) flagging said $i^{th}$ data if said $i^{th}$ data is non-conforming;

e) determining a direction of any signal, shift, or trend indicated by said data array at said $i^{th}$ data;

f) determining if any said signal, shift, or trend is indicated by said $i^{th}$ data stored in said array at said $i^{th}$ data define a statistically significant signal, shift, or trend;

g) determining if a signal, shift, or trend is toward or away from a patient's reference range;

h) determining if a no signal present condition has lasted longer than it should have after an intervention has been initiated;

i) displaying statistics representing said $i^{th}$ data stored in said array;

j) returning to said step (a) when $(i+1)^{th}$ data is available and if a continue process instruction is received; and k) generating a data output signal that represents a statistically significant change in the patient status.

To summarize, an example of one embodiment is a windowed adaptive recursive method for monitoring patient status, and tissue status, by detecting non-conforming data, shifts, and trends in medical sign and lab data, capturing information on medical interventions, comparing the results to the normal value range and/or to a user specified patient reference range, and displaying the results. One embodiment may be described as a windowed adaptive recursive method for monitoring patient status, and tissue status, comprising the steps of: initializing the process; receiving information on medical interventions and medical sign and lab data; detecting changes in incoming medical sign and lab data, calculating a mean and standard deviation if needed from the incoming data or from a baseline data set identified for use in the calculation and identifying and removing non-conforming data points from the data set, calculating various test statistics, testing to determine if the last entered data point is non-conforming, determining the direction of any signal present, determining if any trends and shifts in the data set are statistically significant, determining if detected shifts and trends are toward or away from a reference range, determining if a no change condition has lasted too long, resetting the baseline data set, detecting medical sign data points above or below a normal value threshold, marking the data point above the normal range, within the normal range, and below the normal range, and storing and displaying the data and results for the last window of data points and medical interventions.

Many embodiments give medical caregivers immediate feedback regarding the status of a patient, and facilitate rapid implementation of interventions based on causal relationships between current treatments and medical sign and lab test changes. In view of the practice of transporting less stable patients in combat environments to hospitals in rear echelons, the rapid response facilitated by improved patient monitoring is beneficial because of the greater risk that a patient's condition will change during transport. Also, constraints on medical resources during transit make rapid responses to changes in a patient's condition imperative. Further, a pre-specified integration time or a constant data rate is not required. Therefore, data from unscheduled patient visits and random measurements taken during combat evacuations can be used, rather than requiring measurements to be taken according to a predetermined pattern. Because the methods and algorithms used for implementing various embodiments may be used with low data rates, these embodiments are particularly useful with the limited amounts of data encountered in combat casualty care and ambulatory patient care settings. Various embodiments could also be beneficially utilized for monitoring patients in a critical care facility.

Examples of computer implemented steps for implementing portions of sequence 600 are provided in U.S. patent application Ser. No. 10/423,568, filed 25 Apr. 2003, titled "Method and System for Detecting Changes in Data", which is incorporated herein by this reference. However, it is to be understood that these computer implemented steps may also be written using other programming languages.

B2. Overall Sequence of Operation of Microsensor System

Figure 21A:
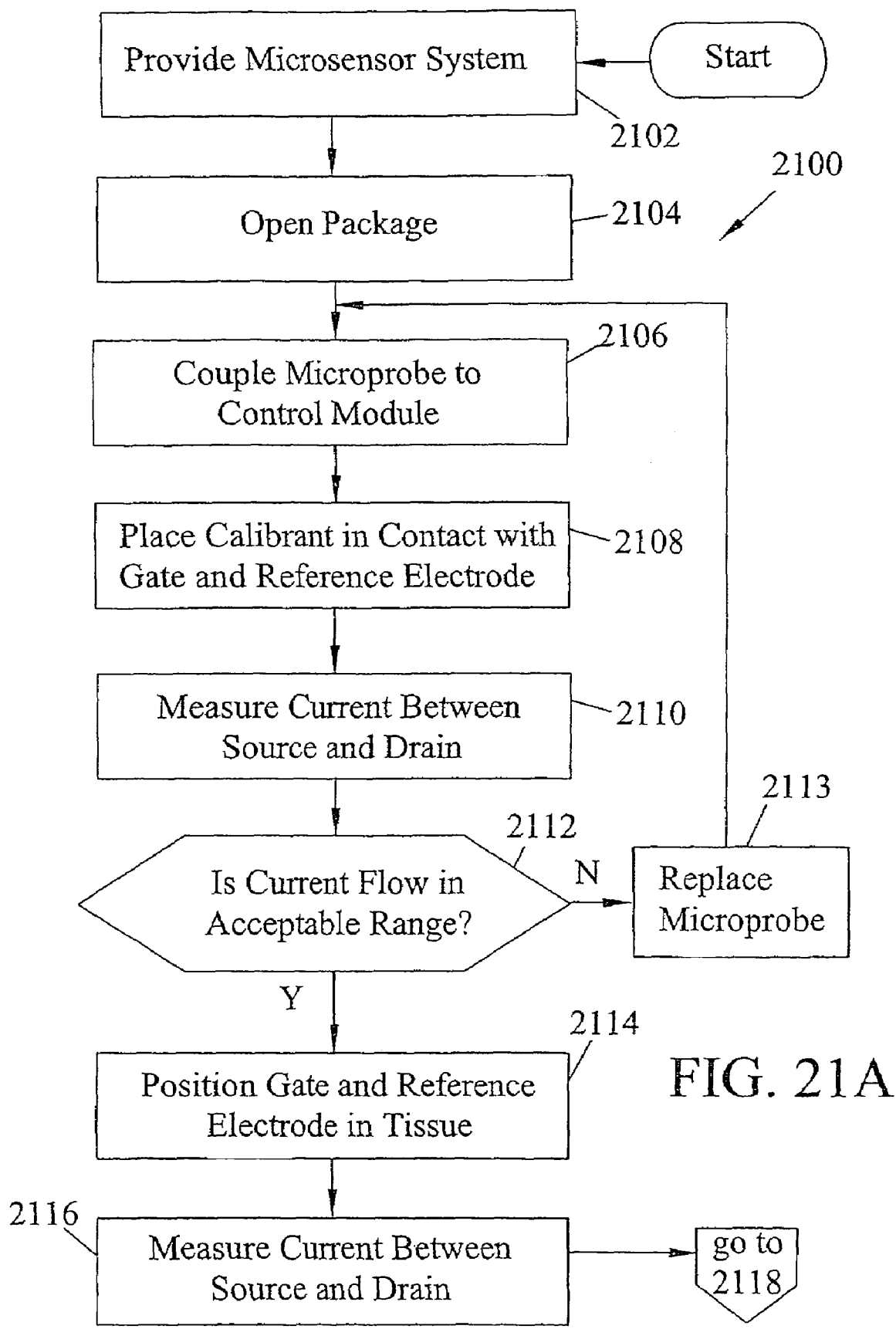
FIGS. 21A-B are a flowchart of an operational sequence for measuring a characteristic of tissue in accordance with an exemplary embodiment.
Figure 21B:
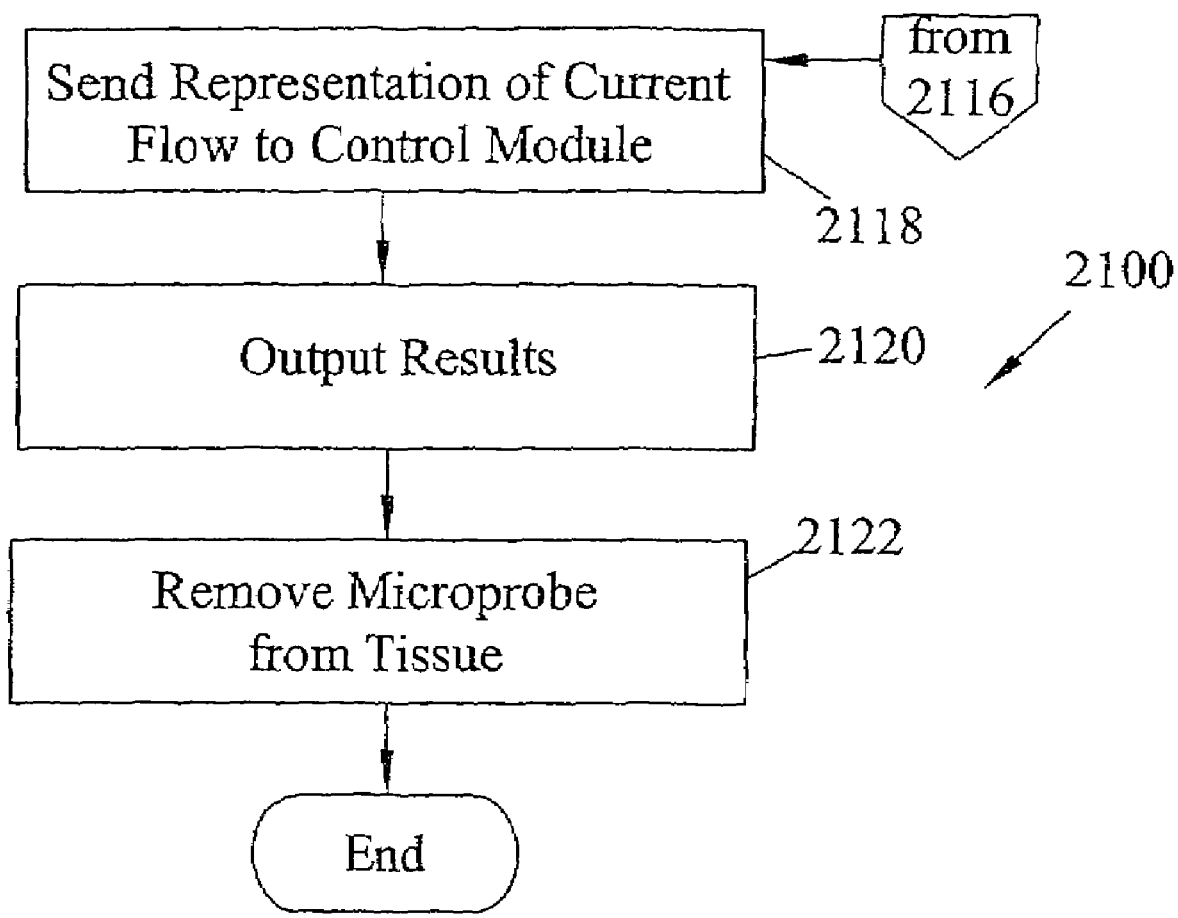

An example of a method embodiment is illustrated in FIGS. 21A-B, which show a sequence 2100 for a method for measuring and/or monitoring one or more characteristics of tissue. As an example, the characteristic may be tissue pH. Additionally or alternatively, the characteristic could be blood gas. Additionally, the temperature of the tissue could also be measured. For ease of explanation, but without any intended limitation, the example of FIGS. 21A-B is described in the context of the microsensor system 1300 described above. The sequence 2100 may begin with operation 2102, which comprises providing the microsensor system 1300. The sequence 2100 may also include operation 2104, which comprises opening a package containing the sterile microprobe 1302 and delivery system 1303, 1702 and removing the sterile microprobe 1302 and delivery system 1303, 1702 for subsequent use. The sequence 2100 may also include operation 2106, which comprises operationally coupling the control module 1304 to the microprobe 1302, for example with electrical wiring. The sequence 2100, may also include operation 2108, which comprises placing a calibrant in contact with the gate 1408 of the ISFET 1406 and with the reference electrode 1410 of the microprobe 1302. Calibration/testing of the microprobe 1302 is performed while the microprobe 1302 is in contact with the calibrant 1418 (which may be positioned within the microprobe delivery system 1303, 1702). The sequence 2100 may also include operation 2110, which comprises measuring the current flow between the source and the drain of the ISFET, as part of the calibration procedure. As part of the calibration/testing of the microprobe 1302, the sequence 2100 may also include operation 2112, which comprises determining if the current flow is in an acceptable range. If the current flow is not in an acceptable range, in operation 2113 the microprobe 1302 may be discarded and replaced with another microprobe 1302, and the process may resume at operation 2106. Built-in test algorithms may also be employed to reconfigure microprobe 1302 as noted previously.

Sequence 2100 may also include operation 2114 which comprises positioning the gate 1408 of the ISFET 1406, and the reference electrode 1410, in tissue of interest (or in contact with, or in fluid communication with the tissue of interest). As an example, operation 2114 may be accomplished by positioning the microprobe 1302 in the tissue of interest by actuating an actuator 1602, 1704 in a microprobe delivery system 1303, 1702. As an example, the tissue of interest may be skin (which may be in a casualty patient). As an example, the microsensor (or microsensors) 1302 may be positioned in the dermis in fingers or toes, which is a useful location for monitoring shock. Alternatively, a microsensor (or microsensors) 1302 could be positioned near the heart to detect heart blockage or congestive heart failure. The microprobe 1302 may be positioned in the dermis generally anywhere on a patient's body.

The sequence 2100 may also include operation 2116, which comprises measuring the current flow between the source 1504 and the drain 1506 of the ISFET 1406. The sequence 2100 may also include operation 2118, which comprises sending a representation of the current flow to the control module 1304. Although a single reading is useful, repeated or continuous monitoring permits performing additional analysis, and permits applying statistical techniques on the data, such as the DCD process discussed above and in the related applications referenced above. Although a single reading from a microprobe 1302 that quickly fails would be useful, a functioning microprobe 1302 could be left in the dermis for a long period of time, for example several days, during which data could be gathered. The microsensor system 1300 may be utilized to provide constant real time information during a medical procedure such as an amputation. In other applications, the microsensor system 1300 may be used to periodically monitor the condition of a patient (for example while warming a patient).

The sequence 2100 may further include operation 2120, which comprises outputting results, which may include a representation of the pH of the tissue (and possibly other information concerning the tissue and analysis of the data). The results could also include any of the output discussed above with reference to the patient status monitor 10. As an example, if multiple microprobes 1302 are simultaneously utilized and monitored by the control module 1304, the results may include a three dimensional representation of the pH of the tissue (and possibly other characteristics of the tissue, such as temperature and/or blood gas levels and/or blood flow information). In a specific example, if multiple microprobes 1302 are positioned in a patient's hand, the results could include a three dimensional display of the hand showing characteristics of the dermis of the hand where the microprobes 1302 are located, and may also display an alert status on the three dimension display. In some examples a volumetric, holographic, stereoscopic or virtual three dimensional display could be employed and manipulated by the user for alternative views.

Thus, whether a single microprobe 1302 or multiple microprobes 1302 are monitored, after the microprobe (or microprobes) 1302 is appropriately positioned within the desired tissue, for example using microprobe delivery system 1303, 1702, tissue pH and/or temperature, as well as, trends, shifts, variance and trends in the variance, of the pH and/or temperature, and/or a trauma score, may be measured, computed, and displayed on the display 1812 of the control module 1304. To perform the analysis of the data received from the microprobe 1302 (or from multiple microprobes 1302), the control module 1304 may perform calculations described above with regard to the patient status monitor 10, and/or described in the related applications referenced above, and/or described in U.S. Pat. No. 5,671,734, issued Sep. 30, 1997, titled "Automatic Medical Sign Monitor", which is incorporated herein by reference. The control module 1304 may also provide an estimate of the probability of the onset of shock and/or death. For example within a user specified period of time based on the application of survival analysis on raw data and/or a trauma score. Depending on the particular hardware arrangement, the calculations and analysis may be performed by the control module 1304, or by the patient status data processor 12, or by the control module 1304 in conjunction with the patient status data processor 12. The sequence 2100 may also include operation 2122, which comprises removing the microprobe (or microprobes) 1302 from the tissue, and disposing of the microprobe 1302 using an acceptable medical waste disposal technique.

V. Other Embodiments

It will be understood that many additional changes in the details, materials, steps and arrangement of parts, which have been herein described and illustrated to explain the nature of the invention, may be made by those skilled in the art within the principle and scope of the invention as expressed in the appended claims. Furthermore, although elements of the invention may be described or claimed in the singular, the plural is contemplated unless limitation to the singular is explicitly stated.

What is claimed is:

1. A microsensor system, comprising:
 a control module; and
 at least one microprobe communicatively coupled to the control module, wherein each microprobe comprises:
 a housing having an aperture;
 an ISFET attached to the housing, wherein the ISFET has a gate located proximate the aperture;
 reference electrode attached to the housing proximate the aperture; and
 a signal bearing medium communicatively coupled to the control module, tangibly embodying a program of machine-readable instructions executable by a digital processing apparatus to perform a method for monitoring a characteristic tissue, comprising:
 means for receiving medical intervention information;
 means for receiving patient reference values;
 means for receiving a tissue data point;
 means for checking validity of said tissue data point;
 means for determining a baseline mean and a baseline standard deviation for said tissue data if the baseline mean and the baseline standard deviation have not been determined for said tissue data;
 means for calculating test statistics;
 means for determining if a condition of said tissue data point is non-conforming;
 means for flagging the condition of said tissue data point if the condition of said tissue data point is non-conforming;
 means for determining if a statistically significant positive or negative trend is occurring; and
 means for generating a data output signal that represents a change in patient status.

2. The microsensor system of claim 1 wherein said tissue data point is selected from the group consisting of: pH, and blood gas.

* * * * *